US 7,419,680 B2

(12) United States Patent
LeGeros

(10) Patent No.: US 7,419,680 B2
(45) Date of Patent: Sep. 2, 2008

(54) CALCIUM PHOSPHATE-BASED MATERIALS CONTAINING ZINC, MAGNESIUM, FLUORIDE AND CARBONATE

(75) Inventor: Racquel Z. LeGeros, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/952,530

(22) Filed: Sep. 28, 2004

(65) Prior Publication Data

US 2007/0082062 A1  Apr. 12, 2007

Related U.S. Application Data

(60) Provisional application No. 60/507,593, filed on Oct. 1, 2003.

(51) Int. Cl.
*A61K 6/033* (2006.01)
*A61K 31/315* (2006.01)
*A61K 33/06* (2006.01)
*A61K 33/10* (2006.01)
*A61K 33/16* (2006.01)
*A61K 33/30* (2006.01)
*A61K 33/42* (2006.01)
*A61F 2/28* (2006.01)
*C01B 25/32* (2006.01)
*C04B 12/02* (2006.01)
*C04B 28/34* (2006.01)

(52) U.S. Cl. .................. 424/423; 424/601; 424/602; 424/603; 424/604; 424/606; 424/641; 424/673; 424/675; 424/676; 424/681; 424/682; 424/686; 424/715; 424/722; 106/690; 106/35; 423/306; 623/23.61; 433/228.1

(58) Field of Classification Search ............... 424/423, 424/601–606, 641, 673, 675, 676, 681–682, 424/722
See application file for complete search history.

(56) References Cited

U.S. PATENT DOCUMENTS

| 4,880,610 | A | 11/1989 | Constantz |
| 4,965,088 | A | 10/1990 | Shimamune et al. |
| 5,141,576 | A | 8/1992 | Shimamune et al. |
| 5,205,921 | A | 4/1993 | Shirkanzadeh |
| 5,211,833 | A | 5/1993 | Shirkhanzadeh |
| 5,258,044 | A | 11/1993 | Lee |
| 5,279,831 | A | 1/1994 | Constantz et al. |
| 5,612,049 | A | 3/1997 | Li et al. |
| 6,037,519 | A | 3/2000 | McKay |
| 6,069,295 | A | 5/2000 | Leitao |
| 6,153,266 | A | 11/2000 | Yokogawa et al. |
| 6,207,218 | B1 | 3/2001 | Layrolle et al. |
| 6,280,789 | B1 | 8/2001 | Rey et al. |
| 6,331,312 | B1 | 12/2001 | Lee et al. |
| 6,346,123 | B1 | 2/2002 | McKay |
| 6,428,803 | B1 | 8/2002 | Ewers et al. |
| 6,585,946 | B1 * | 7/2003 | Bonfield et al. ............ 423/308 |
| 7,351,280 | B2 * | 4/2008 | Khairoun et al. ........... 106/690 |

OTHER PUBLICATIONS

Ajibola, V.O. et al., "Transformation of amorphous calcium phosphate hydroxyapatite in the presence of some ions," Bulletin of the Chemical Society of Ethiopa, 1997, vol. 11(1), pp. 19-24.*
Webster's New World Dictionary, Simon & Schuster, Inc., New York, 1988, p. 1067.*
Genuis, S.J. et al., "Picking a bone with contemporary osteoporosis management . . ." Clinical Nutrition, 2007, vol. 26, pp. 193-207.*
Daculsi, G. et al., "Current state of the art biphasic calcium phosphate bioceramics," Journal of Materials Science, Mar. 2003, vol. 14(3), pp. 195-200.*
Legeros, R.Z. et al., "Biphasic calcium phosphate bioceramics: preparation, properties and applications," Mar. 2003, vol. 14(3), pp. 201-209.*
Julien, M. et al., "Physico-chemical-mechanical and in vitro biological properties of calcium phosphate cements with doped amorphous calcium phosphates," Biomaterials, Feb. 2007, vol. 28(6), pp. 956-965.*
Legeros, R.Z. et al., Fluoride-cation interaction in the formation and stability of apatites. Journal of Fluorine Chemistry, 1988, vol. 41, No. 1 pp. 53-64.
Manjubala, T.S. et al., Preparation of Biphasic calcium phosphate doped with magnesium fluoride for osteoporotic applciations, Journal of Materials Science Letters, 2001, vol. 20, No. 13, pp. 1225-1227.
Legeros, R.Z., Properties of osteoconductive biomaterials: calcium phosphates, Clinical Orthopaedics and Related Research, Feb. 2002, No. 395, pp. 81-98.

* cited by examiner

*Primary Examiner*—John Pak
(74) *Attorney, Agent, or Firm*—Klauber & Jackson

(57) ABSTRACT

Compositions useful in the prevention and treatment of osteoporosis and for bone and fracture repair. Slow-releasing calcium phosphate-based materials are disclosed, incorporating Mg, Zn, F and carbonate, which will promote bone formation and inhibit bone resorption and thus be agents for the cited uses.

9 Claims, 9 Drawing Sheets

Effect of BCPs on Proliferative Capacity of Human Osteoblasts

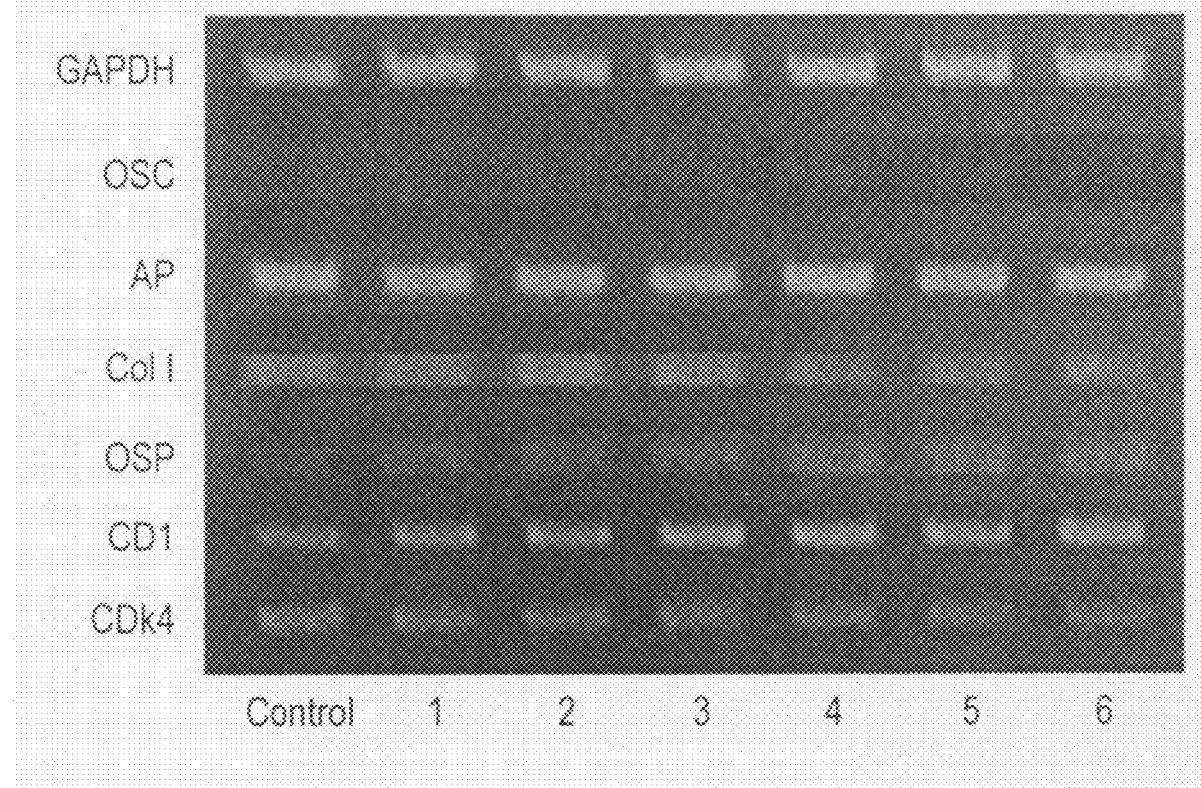

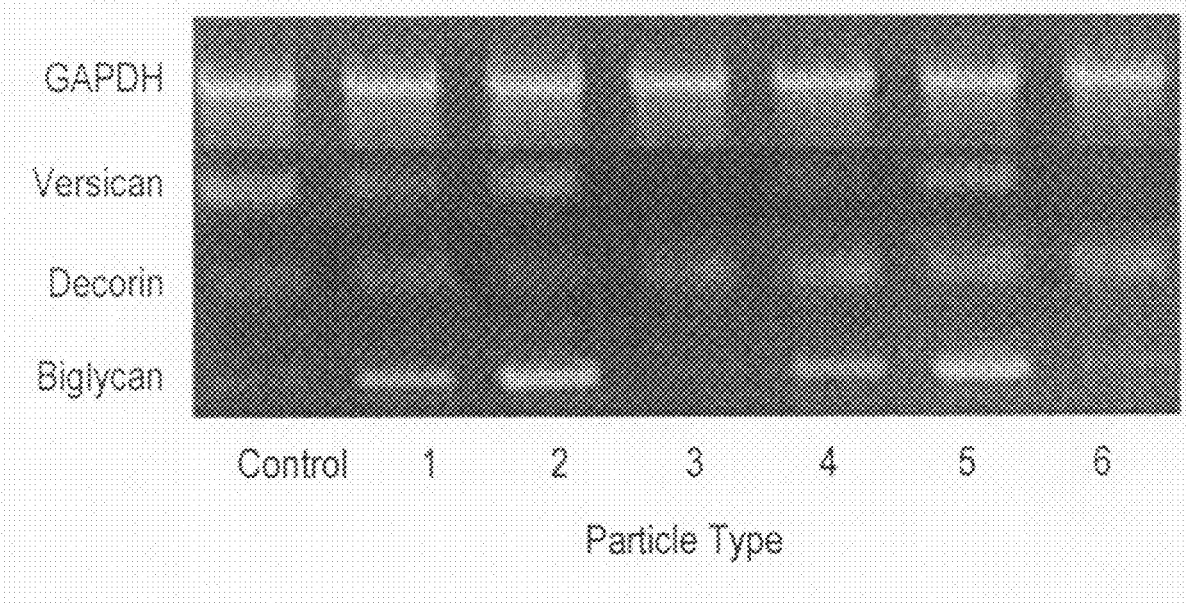

CALCIUM PHOSPHATE-BASED MATERIALS CONTAINING ZINC, MAGNESIUM, FLUORIDE AND CARBONATE

RELATED APPLICATIONS

This application claims priority from U.S. Provisional Patent Application Ser. No. 60/507,593, filed Oct. 1, 2003.

FIELD OF THE INVENTION

This invention relates generally to compositions and methods useful in the prevention and treatment of osteoporosis and for bone and fracture repair. More specifically, the invention relates to slow-releasing calcium phosphate-based materials incorporating Mg, Zn, F and carbonate, which will promote bone formation and inhibit bone resorption and thus be agents for the cited uses.

BACKGROUND OF THE INVENTION

Osteoporosis is a progressive and debilitating metabolic bone disease characterized by low bone mass (bone loss) and structural deterioration (thinning of the cortical bone and disorganization of the trabecular bone) leading to increased bone fragility and susceptibility to fractures especially of the hip (femoral head), spine (vertebrae) and the wrist. Osteoporosis is a 'silent' disease because related bone loss occurs without symptoms until the individual suffers a bone fracture. Worldwide, the number of hip fractures due to osteoporosis was projected to rise from 1.7 million in 1990 to 6.3 million by 2050. In the U.K., it was estimated that the National Health Service cost associated with osteoporosis is over L600 million ($1.02 billion) per year in 1991 and projected to increase considerably. In Japan, estimated number of hip fracture in 1998 was about 90,000/year with associated hospital cost of about $120 million per year. In the U.S., osteoporosis is responsible for more than 1.5 million fractures/year including: 300,000 hip fractures and approximately 700,000 vertebral fractures, 200,000 wrist fractures and 300,000 fractures in ribs and other sites. 12% to 20% of patients with hip fracture die within a year after the fracture, usually from complications related to either the fracture or surgery. In 2001, the estimated health care cost (hospitals and nursing homes) related to osteoporosis and associated fractures were $17 billion ($47 million/day!) and projected to increase to $30 to $40 billion annually in the next decade.

Bone tissue consists of two types: cortical (or compact bone) and trabecular (or spongy bone), differing in architecture, properties and function. The cortical bone provides mechanical strength and protective functions while cancellous or trabecular bone provides the metabolic functions. Two major processes are responsible for the development and maintenance of the bone tissue: bone formation (bone build-up) and bone resorption (bone modeling). During skeletal development in humans (birth to adulthood), the rate of bone formation is much greater than the rate of bone resorption until maximum bone mass (peak bone mass) is reached (at about age 35 for cortical bone and earlier for trabecular bone). After the peak bone mass is reached, the bone turnover per year is about 25% in trabecular bone and 3% in cortical bone. A bone remodeling process (bone turnover) in which the rates of bone formation and bone resorption are equal in the same site maintains the skeletal mass in adulthood. When these two processes are in equilibrium or are "coupled", there is no net gain or loss in bone mass. It is believed that the bone loss associated with primary type of osteoporosis results from the uncoupling of these two processes; with the rate of bone formation being much lower than the rate of resorption. A secondary type of osteoporosis is observed after prolonged immobilization and prolonged periods of bed rest or under glucocorticoid treatment for pulmonary disorders. In such conditions the mechanism of bone loss include both increased bone resorption and decreased bone formation. Reduction in bone formation leads to inadequate bone replacement during remodeling and to gradual bone loss resulting in the thinning of the cortical bone and reduction in cancellous bone formation.

Two major bone cells are involved: osteoblasts for bone formation and osteoclasts for bone resorption. Bone formation is reflected in osteoblast activities involving matrix (collagen, protein, DNA) formation and mineralization. Bone resorption is determined by the rate of osteoclast recruitment and the intensity of osteoclast activity manifested by the appearance of resorption pits. Most conditions leading to osteoporosis (including estrogen deficiency, hyperparathyroidism and hyperthyroidism) are associated with increased osteoclastic bone resorption and the inability of the bone formation process to keep up with the resorption process.

Bone is a composite of about 25 wt % biopolymer (organic matrix), 70 wt % mineral or inorganic phase, and 5 wt % water. The organic matrix is principally (about 95%) of Type I collagen with non-collageneous proteins. Osteoporosis is characterized by bone loss, decreased bone strength, lower bone density, poorer bone quality (e.g., porous cortical bone), thinning cortical bone and disorganized trabecular bone. Bone loss is often a predictor of future fracture risk.

In bone resorption, dissolution of the bone mineral occurs before the degradation of the collagen fibers. The rate of osteoclastic destruction of mineralized tissues was observed to be inversely proportional to bone mineral density. The bone mineral or inorganic component of bone is a calcium phosphate idealized as a calcium hydroxyapatite, $Ca_{10}(PO_4)_6(OH)_2$. However, comprehensive studies on synthetic and biologic apatites demonstrate convincingly that biologic apatites (mineral phases of enamel, dentin, cementum and bone) are apatites containing minor constituents (carbonate and magnesium) and are more accurately described as carbonate hydroxyapatite, approximated by the formula, $(Ca,Na,Mg)_{10}(PO_4,HPO_4,CO_3)_6(OH)_2$. Changes in the composition of the apatite affect its lattice parameters, morphology, crystallinity (reflecting crystal size and/or perfection) and dissolution properties. For example, Mg-for-Ca or $CO_3$-for-$PO_4$ substitution decreases crystallinity (crystal size) and increases solubility while F-for-OH substitution increases crystal size and decreases the solubility of synthetic apatites.

Osteoporotic bones from patients have been reported to have lower magnesium (Mg) and carbonate ($CO_3$) concentrations. Along with decreased Mg and $CO_3$ contents, larger bone apatite crystals (based on infrared spectroscopic measurements of 'crystallinity index') were reported in bones from patients with postmenopausal osteoporosis and alcoholic osteoporosis. Smaller bone apatite crystals were observed in bones of rats fed excess Mg while bone apatite crystals increased in size in bones from Mg-deficient rats. Enamel crystals of rats injected with Mg were smaller than those of the controls. On the other hand, bone apatite crystals from rats drinking high levels of fluoride (F) were larger and less soluble. Increase in width of bone apatite crystals were also observed in the bones of F-treated rabbits. Larger enamel apatite crystals in rat's teeth were observed after F administration.

Although there is still no known cure for osteoporosis, some medications have been approved by the FDA for postmenopausal women to prevent and/or treat osteoporosis. These include biphosphonates such as alendronate (Fosamax) and Risedrnate (Actonel), Calcitonin (e.g., Miacalcin), estrogen (e.g., Climara, Estrace, Estraderm, Estratab, Ogen, Orto-Es, Viovlle, Premarin, etc) and hormones (estrogens and progestins (e.g., Activella, FemJHrt, Premphase, Prempro, etc); and selective estrogen receptor modulators, SERMs such as ralozifene (Evista). Sodium fluoride (NaF) treatment is pending approval. Treatments under investigation include parathyroid hormone (PTH), vitamin D metabolites, other biphosphonates, and SERMs. These therapeutic agents, except F therapy, are described as anti-resorptive agents because they principally target bone resorption. These therapeutic agents are associated with some serious side effects.

Fluoride therapy. The effect of fluoridated water on lowering the incidence of dental caries is well documented and has been the basis of fluoridation of oral care products (e.g., dentifrices, mouthrinses, topical gels, post-natal tablets). Reports on effect of fluoridated water on the prevalence of osteoporosis have been contradictory and inconclusive. Currently, experimental fluoride compounds recommended for osteoporosis therapy include sodium fluoride (NaF), mono-sodiumfluorophosphate, MFP, ($Na_2PO_3F$) and slow release preparation of NaF (SR—NaF). There is general agreement that F stimulates bone formation directly without the need for prior bone resorption and that it is this uncoupling of resorption and formation that makes this element so effective in increasing bone mass.

Calcium (Ca). The bone mineral can best be described as a carbonate hydroxyapatite, approximated by the formula: $(Ca, Na, Mg)_{10}(PO_4, CO_3, HPO_4)_6 (OH, Cl)_2$ containing about 40% calcium. Calcium is stored in bone in the process of mineralizing newly deposited tissue and it is withdrawn from bone only by resorption of old bone tissue. The biological fluids are metastable with respect to apatite, maintaining the integrity of the bone and tooth mineral (apatite). Ca deficiency in the diet induces osteoporosis in rats. Ca supplementation is strongly recommended for optimum bone health. Ca supplementation has been reported to reduce cortical bone loss during the first 5 years of menopause and produce a sustained reduction in the rate of total body bone loss at least 3 years after menopause. However, by itself, Ca supplementation does not appear to slow the rapid loss of trabecular bone during the first few years of menopause nor does it prevent the menopause-related lumbar bone loss. A study on spinal bone loss in postmenopausal women supplemented with Ca and trace minerals (zinc, manganese and copper) showed that bone loss was arrested by intake of Ca plus trace minerals while no difference was observed between the placebo group or group receiving Ca alone.

Magnesium (Mg). Magnesium (Mg) is an important element in biological systems. 50% to 60% of Mg in the body is associated with the bone mineral. The rest of the Mg in the body is intracellular, a required co-factor in more than 300 enzyme systems. Mg is critical for cellular functions that include oxidative phosphorylation, glycolysis, DNA transcription and protein and nucleic acid synthesis. Mg deficient diet in rats was shown to have impaired bone growth (reduction in bone formation and bone volume), decreased bone strength and increased fragility. These and other animal studies implicate Mg deficient diet as a possible risk factor for osteoporosis. In humans, Mg deficiency in the diet was also associated with osteoporosis. Mg therapy was reported to increase bone mass in postmenopausal osteoporosis. Other studies suggest that Mg supplementation suppresses bone turnover rates in young adult males. On the cellular level, in vitro, an isolated report indicates that Mg directly stimulated osteoblast proliferation.

On the bone apatite crystal level, Mg and $CO_3$ content were lower in osteoporotic compared to normal human bone and bone with decreased Mg had larger apatite crystals. Also, bone and enamel apatite crystals were smaller in rats fed with Mg supplement while bone apatite crystals in Mg deficient rats were larger than those in control. Such observations are consistent with the effect of Mg on the formation of synthetic apatites: promoting the formation of apatite with low crystallinity and higher solubility. At higher solution Mg/Ca, Mg-substituted tricalcium phosphate (b-TCMP or Mg-TCP) or amorphous calcium phosphate (ACP) forms at the expense of apatite.

Zinc (Zn). Zn is an essential trace element in the activity of more than 300 enzymes and affects basic processes of cell division, differentiation, and development and is required in collagen biosynthesis and in the biosynthesis and repair of DNA, in matrix and protein synthesis and plays an important role in bone metabolism and growth. It is the most abundant trace metal in bone mineral, being present at a concentration of up to 300 ppm. Zn deficiency in rats was shown to result in a 45% reduction in cancellous bone mass and to a deterioration of trabecular bone architecture, with fewer and thinner trabeculae and therefore may be considered as a risk factor in the development of osteoporosis. In vivo, Zn was shown to stimulate bone formation in weanling rats and in aged rats.

On the cellular level in vitro, Zn has been shown to have a stimulatory effect on bone formation and an inhibitory or biphasic effect on osteoclastic bone resorption. Studies on Zn-releasing compounds such as b-alanyl-L-histadanato zinc and Zn-TCP demonstrated that Zn promoted greater bone formation in vitro and was effective in increasing bone density or in preventing bone loss in vivo.

On the crystal level in synthetic systems, the presence of Zn causes the formation of apatite with low crystallinity, promoting the formation of Zn-substituted β-TCP or even amorphous calcium phosphate (ACP), depending on the solution Zn/Ca molar ratio. Both Mg and Zn were shown to inhibit the growth of apatite.

The relevant literature suggests that Mg or Zn separately may have beneficial effects on bone matrix but may cause the formation of bone apatite with low crystallnity (small crystal size). On the other hand, F may improve crystallinity (larger crystal size) and reduce solubility of bone apatite, but may cause impaired or abnormal mineralization. Separately, Mg, Zn and F ions have been associated with promotion of bone formation and/or inhibition of osteoclastic activity (resorption)—but to the best of applicant's knowledge have not in the past been considered in combination.

SUMMARY OF THE INVENTION

The novel biomaterials of the present invention combine concentrations of Mg, Zn and F ions in a carbonate-containing biphasic calcium phosphate (BCP) system. The biomaterial is not considered to have serious side effects or deleterious effects on bone strength and fracture incidence such as those associated with the presently FDA-approved anti-resorptive agents. The biomaterial of the invention has the following advantages: (1) similarity in composition to the bone mineral (which is a carbonate apatite); (2) slow release of Mg, Zn, F, Ca, and P ions; (3) combines ions in preferred concentrations known separately to promote bone formation and minimize or prevent bone resorption; (4) allows the incorporation of lower levels of these ions thus avoiding deleterious effects observed with higher levels; (5) has the beneficial effects of Mg and Zn on collagen and protein formation to balance the F effect on bone apatite formation and crystal size, promoting formation of bone with higher mineral density and greater bone mass; (6) has synergistic effects of the three elements on bone resorption to allow the rate of bone formation to catch up with the rate of bone resorption, resulting in a net gain in bone mass. Thus the said materials are deemed useful for the following applications: (a) reduction in the development of osteoporosis (prevention), (b) increase cancellous bone mass and arresting the progress of osteoporosis (therapy), and (c) repairing of the fracture caused by osteoporosis (bone repair and regeneration). The preparation of the novel biomaterial is innovative in its simple but rational approach.

Biphasic calcium phosphate, BCP, is a term presently used to describe an intimate mixture of unsubstituted hydroxyapatite (HA) and unsubstituted β-TCP, $Ca_3(PO_4)_2$. BCP of varying HA/β-TCP ratios is obtained by sintering calcium-deficient apatite (Ca/P<1.67) that has been prepared either by precipitation or hydrolysis method or by solid-state reaction. Unsubstituted β-TCP does not form from solutions and can only be obtained by sintering Ca-deficient apatite, Ca/P=1.5, or by solid state reaction between $CaHPO_4$ and $Ca(OH)_2$. However, when Mg or Zn ions are present in the solution, Mg- or Zn-substituted β-TCP can form because Mg- or Zn-incorporation stabilizes β-TCP structure. For this reason, Mg-substituted β-TCP (β-TCMP or Mg-TCP) occurs in biological systems, usually in pathological calcifications or diseased states.

The limit of Mg or Zn incorporation in β-TCP is higher than that in the apatite. The applicant has found that incorporation of these ions in the apatite may be increased when carbonate or fluoride ions are present in the solution. The incorporation of carbonate ($CO_3$-for $PO_4$ coupled with Na-for-Ca) in the apatite can be maximized to 22 wt % (3 moles) depending on the solution carbonate/phosphate (C/P) molar ratio. The maximum F-for-OH substitution in the apatite is about 3.8 wt %.

The useful range (by weight %) of components in the biomaterials of the invention are as follows:

Mg: 0.5 to 12 wt %; Zn: 1 to 12 wt %; F 0.1 to 4 wt %; calcium (Ca commonly designated "C" herein as in "TCP" or "BCP"): 20 to 40 wt %; phosphate (commonly designated "P" herein, as in "TCP" or "BCP")=10 to 20 wt %; carbonate ($CO_3$): 1 to 20 wt %. Every formulation will contain Ca, P, and $CO_3$. The biomaterial of the invention may also be combined with organic moieties known to inhibit osteoclast activity. The biomaterial may be unsintered or highly sintered. It may be used as a diet supplement or as bone-graft material or scaffold for tissue engineering. The biomaterial may be in any of the following forms; powder, granules, blocks, in a carrier (e.g., saline solution, polymer solution) for injection at local sites, and may be incorporated in an injectable cement.

BRIEF DESCRIPTION OF DRAWINGS

In the drawings appended hereto:

FIG. 8 shows the effect of the present synthetic materials on the phenotype expression; and FIG. 9 shows the effect of BCPs on proteoglycons expression of human osteoblasts.

DESCRIPTION OF PREFERRED EMBODIMENTS

In the present invention well-characterized Mg/Zn/F-BCP materials in powder (of known surface area) or disc forms are used.

Mg/F-BCP, Zn/F-BCP, Mg/Zn/F-BCP were prepared by precipitation at 90° C. from solutions with known solution Mg/Ca, Zn/Ca, C/P and F/P. X-ray diffraction (XRD) analysis confirmed earlier observations on the effect of Mg or Zn on the crystallinity of the apatite (FIG. 1), i.e., Mg or Zn tends to lower the crystallinity of apatite.

Figure 1:
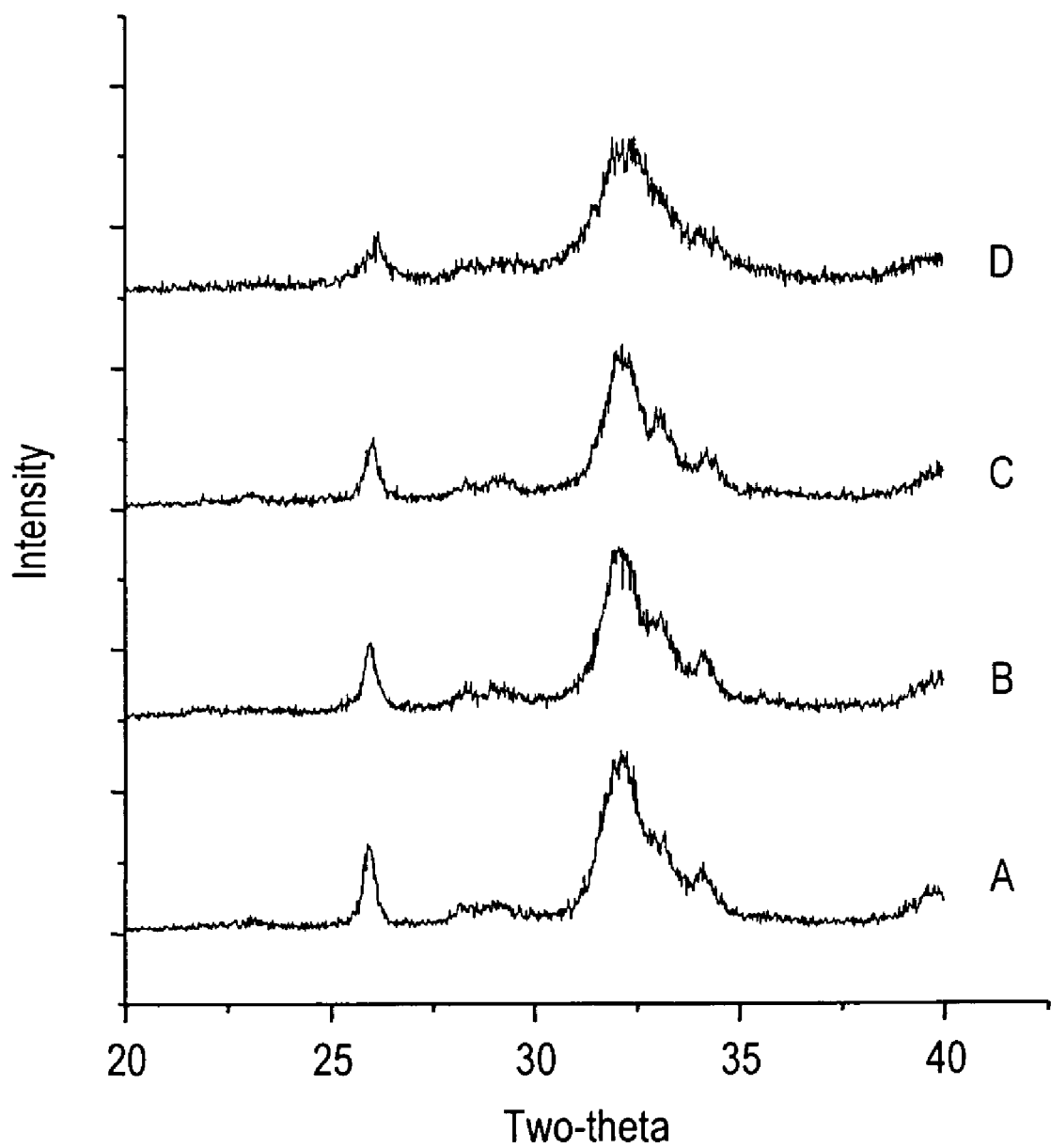
FIG. 1 is a graph depicting XRD patterns of precipitated carbonate apatite which has been substituted with ion combinations in accordance with the invention.

In FIG. 1 XRD patterns appear of precipitated carbonate apatite containing: (A) F, (B) Mg+F; (C) Zn+F; and (D) Mg+Zn+F. The differences in the sharpness of the diffraction peaks (line broadening) at about 25.8 deg 2 q reflect the difference in their crystallite size. Mg and Zn have additive effects on reducing crystallinity of apatite (B & C vs D).

Figure 2:
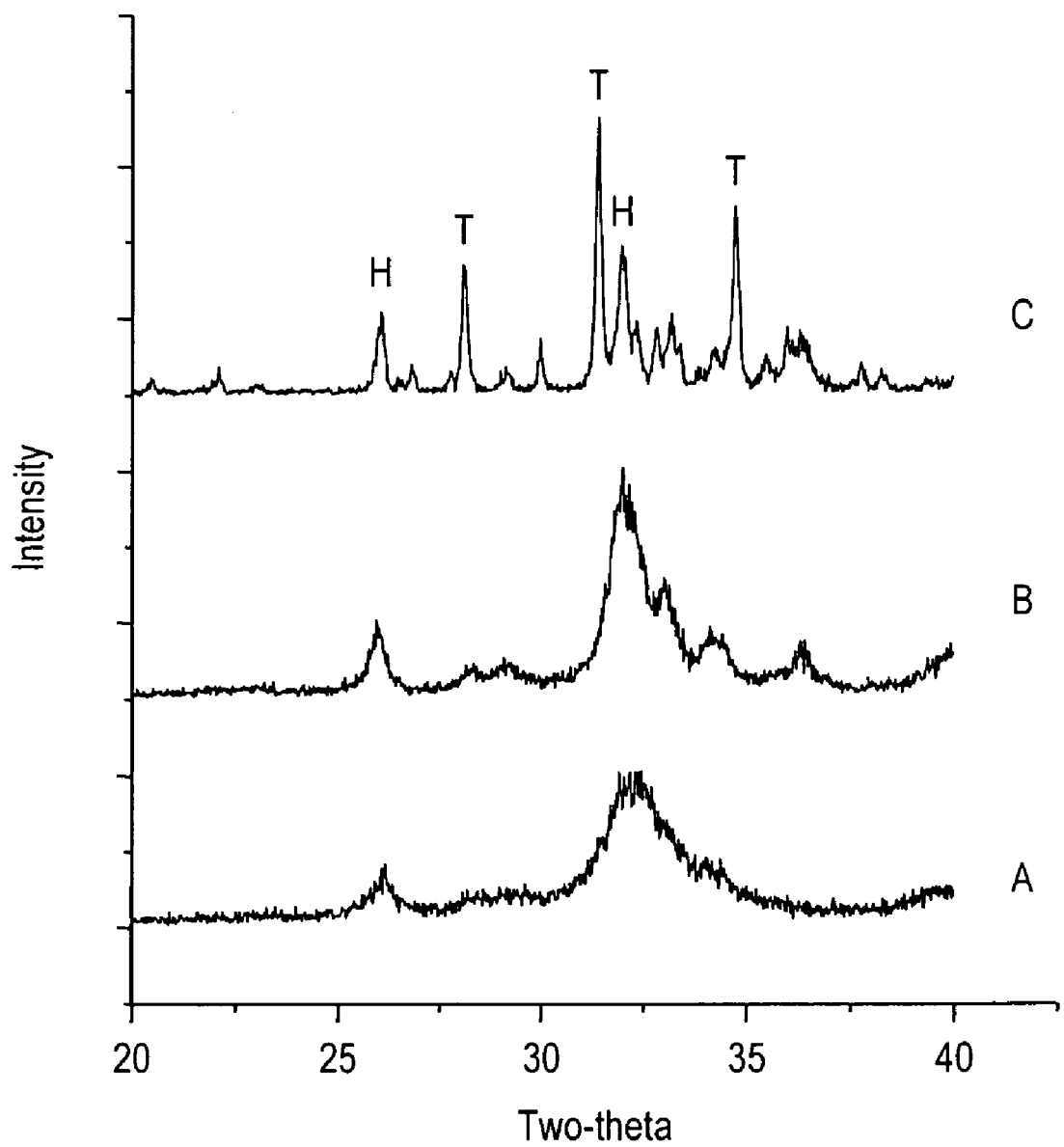
FIG. 2 is a graph showing XRD patterns of Mg/Zn/F-BCP before and after sintering.

In FIG. 2 XRD patterns of Mg/Zn/F-BCP appear: (A) before sintering and after sintering at (B) 600° C.; and (C) 800° C. T=Mg- and Zn-substituted βTCP; H=F-substituted apatite.

Figure 3A:
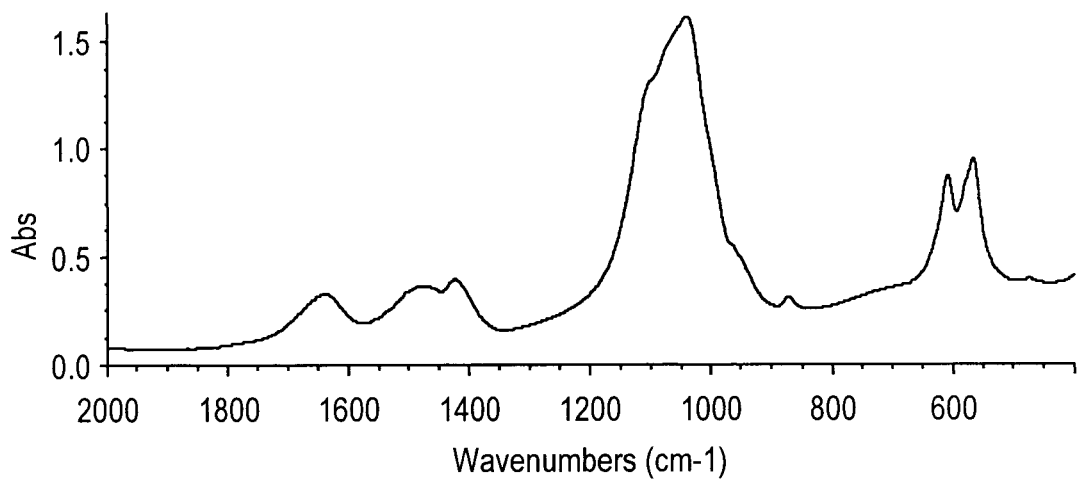
FIG. 3 depicts FTIR spectra for materials in FIG. 2, showing reduction in $CO_3$ content.
Figure 3B:
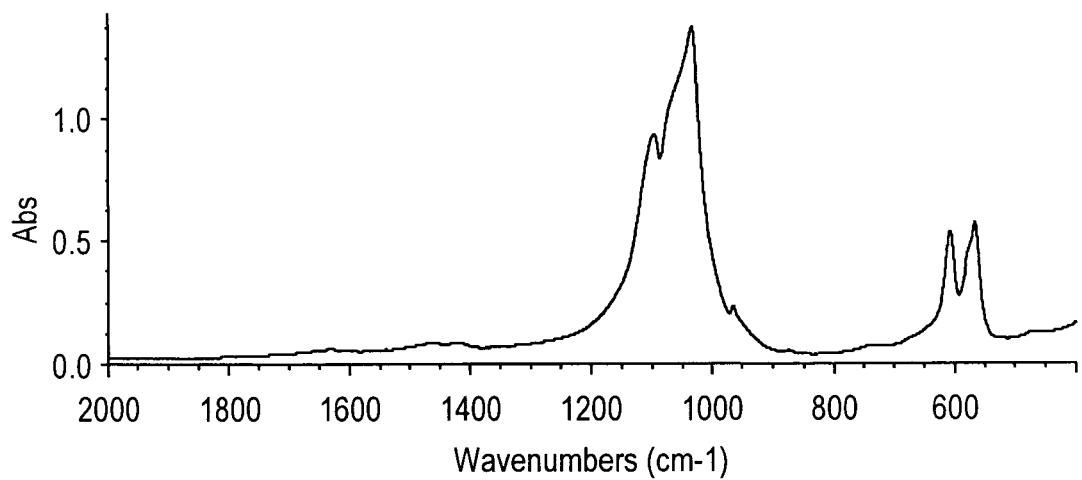
Figure 3C:
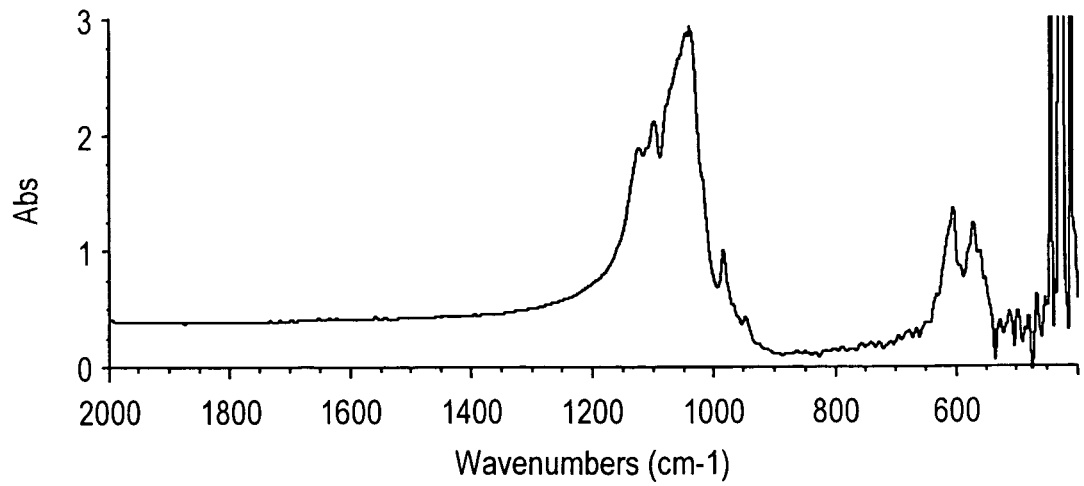

In FIG. 3 FTIR spectra appear of materials (A) before and after sintering (B) 600° C. and (C) 800° C. showing reduction in $CO_3$ content (absorption bands at about 1400 to 1570 $cm^{-1}$).

Figure 4:
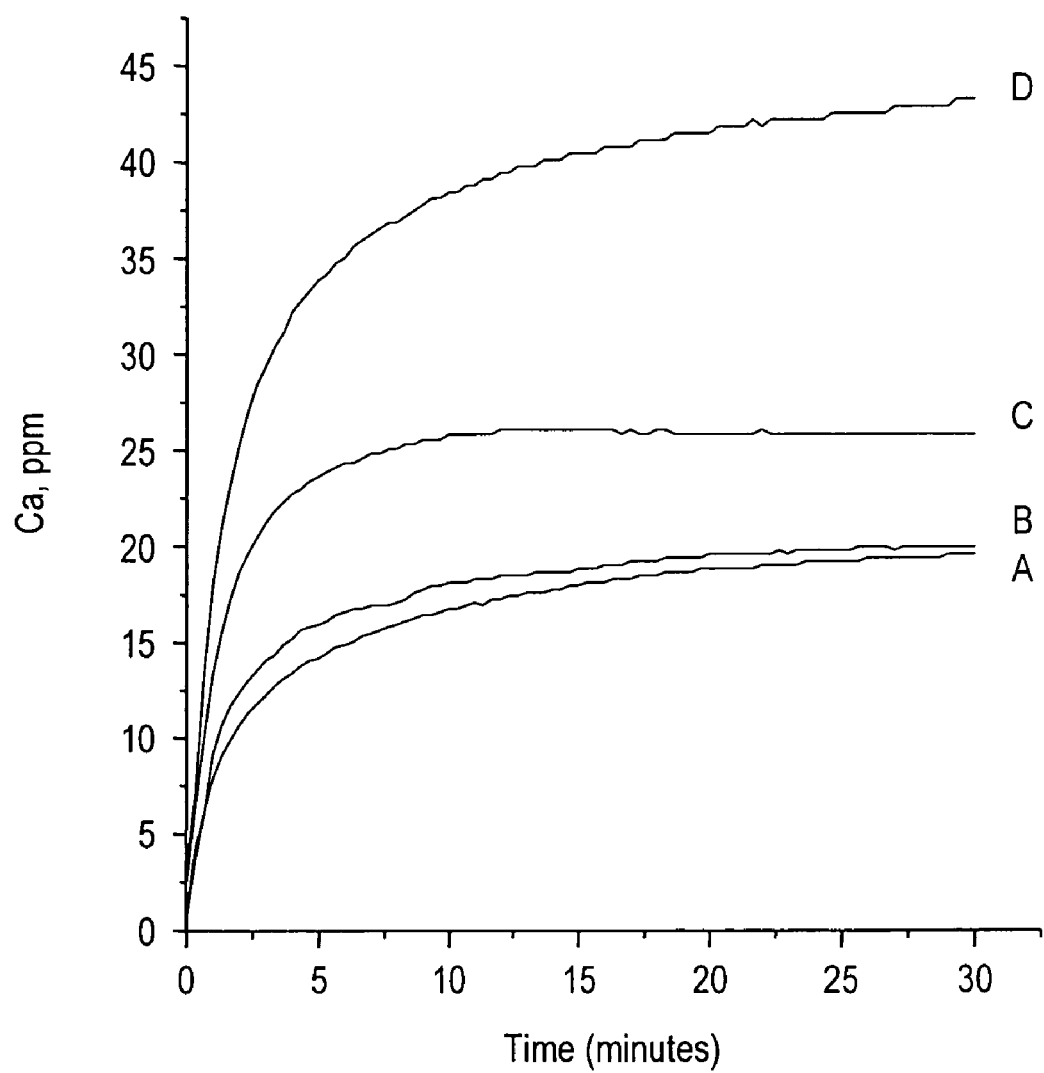
FIG. 4 depicts release of Ca ions with time of the synthetic materials: (A) CFA; (B) Zn/F-BCP; (C) Mg/F-BCP and (D) Mg/Zn/F-BCP.

FIG. 4 depicts release of Ca ions with time of synthetic materials: (A) CFA; (B) Zn/F-BCP; (C) Mg/F-BCP and (D) Mg/Zn/F-BCP showing the additive effects of Mg and Zn (D) on the dissolution properties. The calculated d[Ca]/dt (ppm/min) are: (A) 2.54; (B) 2.86; (C) 4.15 and (D) 6.29. Mg and Zn have additive effects on increasing the initial dissolution rates.

Figure 5:
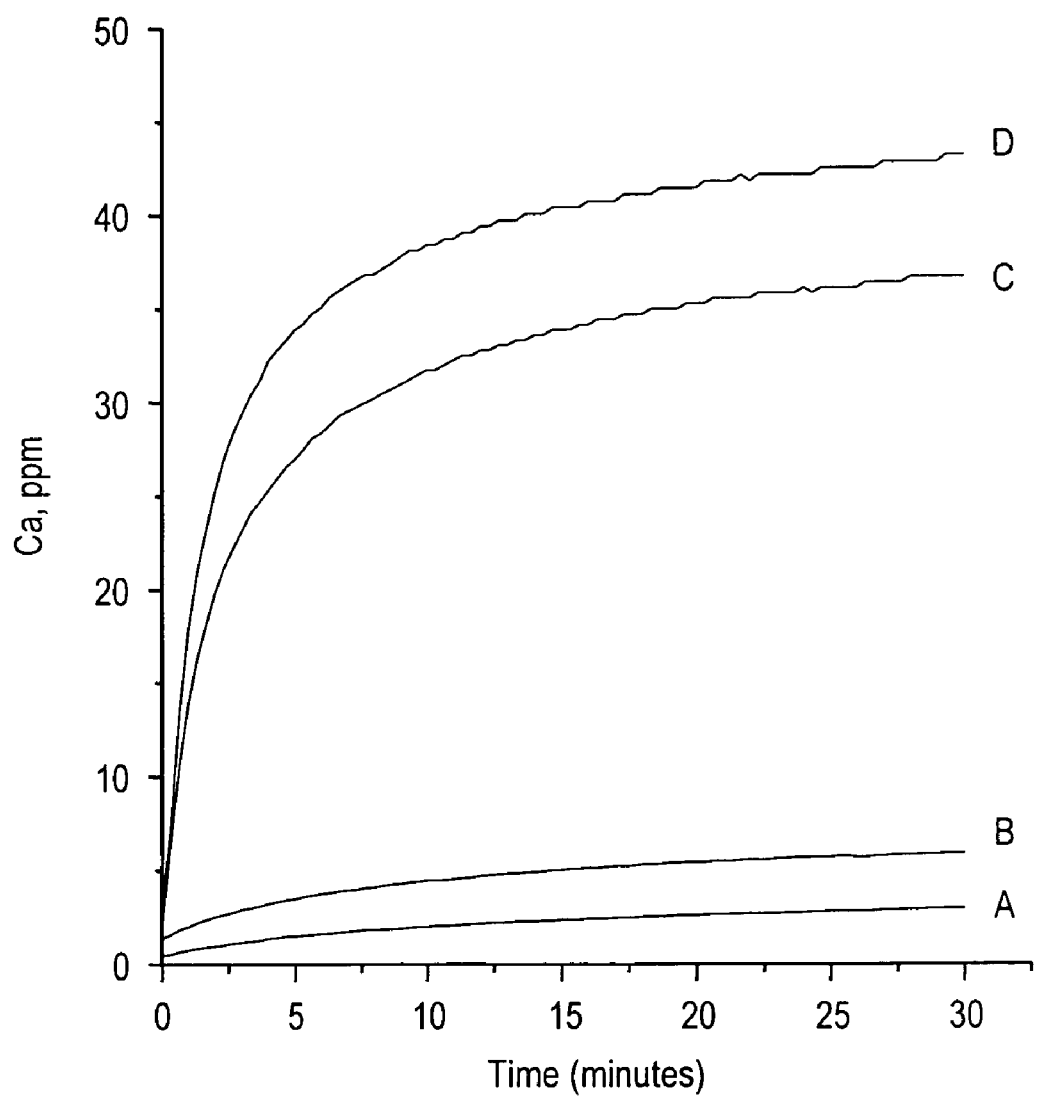
FIG. 5 depicts release of Ca ion with time of Mg/Zn/F-BCP before (C, D) and after ignition at 600° C. (B) and at 800° C. (A)

FIG. 5 depicts release of Ca ion with time of Mg/Zn/F-BCP before (C, D) and after ignition at 600° C. (B) and at 800° C. (A). C and D have similar concentrations of Mg and Zn but different concentrations of F, with (D) having the lower F concentration. The initial dissolution rate is decreased with increasing sintering temperature (A and B vs. C and D) and with increasing F concentration (A vs. B, C vs. D).

Figure 6:
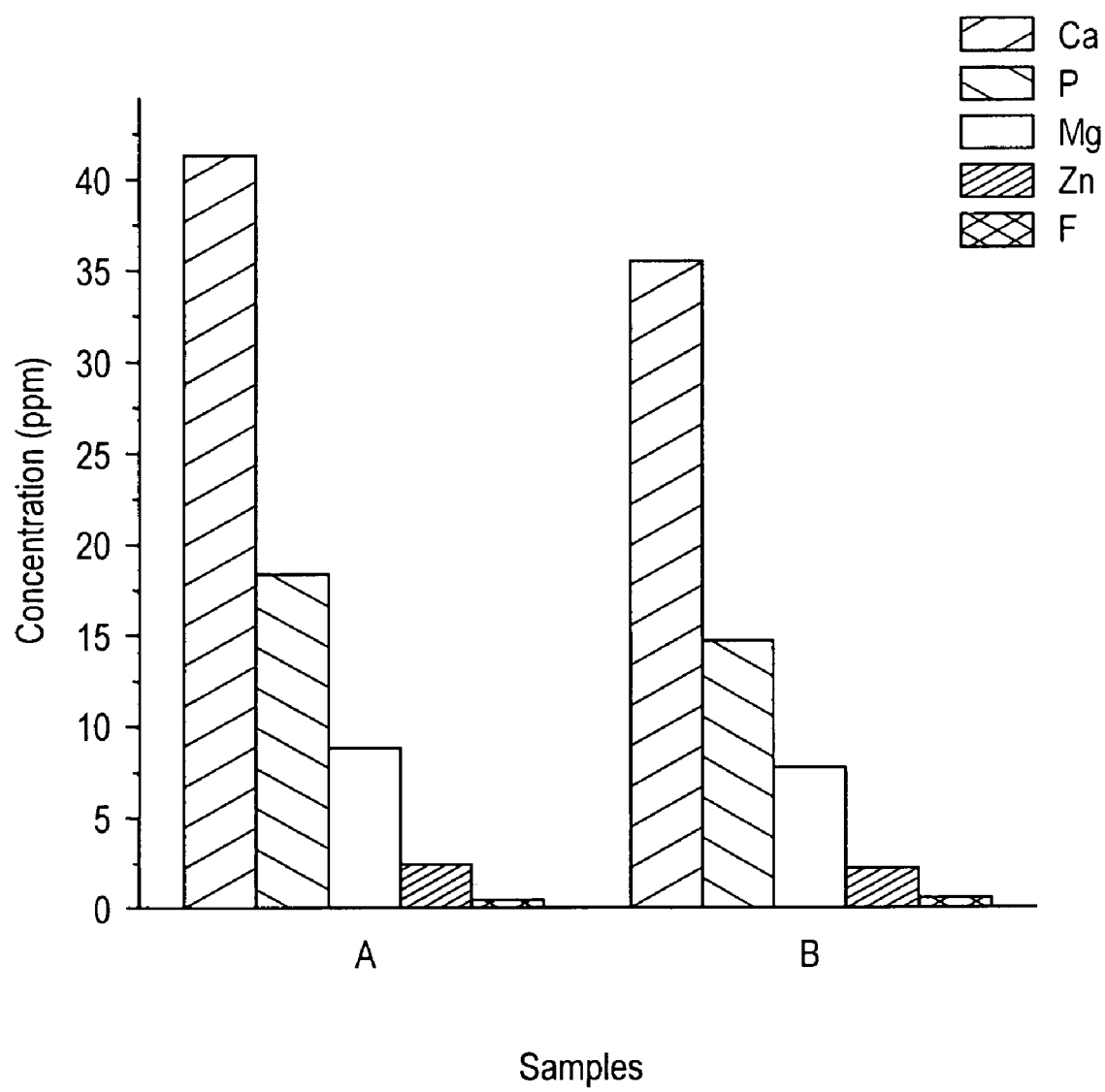
FIG. 6 depicts release of Ca, P, Mg, Zn and F after 30-min exposure in acidic buffer.

FIG. 6 depicts release of Ca, P, Mg, Zn and F after 30-min exposure in acidic buffer (0.1M NaAc, pH 5, 37° C. Samples A and B have similar Mg and Zn concentrations. F concentrations (wt %): (A) 0.68 and (B) 1.20.

Elemental analyses using inductive coupled plasma (ICP) showed that the amount of Mg, Zn or F incorporated in the precipitated apatite depended on the solution concentrations of these ions. Sintering at 600° C. increased the crystallinity (crystal size) and at 800° C., resulted in the formation of biphasic calcium phosphate, BCP, consisting of a mixture of Mg- and Zn-substituted b-TCP, T, and F-substituted apatite, H, (FIG. C9) based on the lattice parameters. Sintering reduced the amount of $CO_3$ in the apatite as shown by the loss of absorption bands between 1400 and 1550 cm$^{-1}$ (FIG. C10). Incorporation of Mg or Zn increased while incorporation of F decreased extent of dissolution as measured by the Ca release (FIG. 4). The extent of dissolution decreased with increasing sintering temperature and with increasing amount of F (FIG. 5). The levels of Mg, Zn, F, Ca and P ions released after 30-minute suspension in the acidic buffer (0.1M NaAc, pH 5, 37° C.) as shown in FIG. 6. Maximum release was observed after 5-min exposure in the acidic buffer.

Based on the above it is seen that Mg/Zn/F-BCP in biologically active concentrations of Mg, Zn or F ions is prepared. In the Mg/Zn/F-BCPs, the crystallinity and release of the ions can be adjusted by manipulation of reaction and sintering parameters.

EXAMPLES

Cell Response to Mg/Zn/F-BCP Materials

Unsintered materials used for the below were: carbonate-hydroxyapatite (CHA), Mg-containing CHA (Mg/CHA), Zn-containing CHA (Zn/CHA); F-containing CHA (CFA); Mg-, Zn- and F-containing CHA with Mg- and Zn-containing β-TCP (Mg/Zn/F—BCP). The purpose of this study is to determine the cell response to these materials.

(a) Effect on proliferative capacity: The effect on proliferative capacity of human osteoblast-like cells was studied by incubating human MG-63 ($10^5$ cells/well/ml) in the presence or absence of materials at 37° C., 5% $CO_2$ for 5 days. The cells were radiolabeled with 1 mCi of $^3$H-thymidine and the proliferation rate was determined by scintillation counting of TCA precipitable DNA. The materials significantly increased the proliferative capacity of osteoblast-like cells. Higher proliferative effect compared to control in cells exposed to the synthetic materials was observed.

Figure 7:
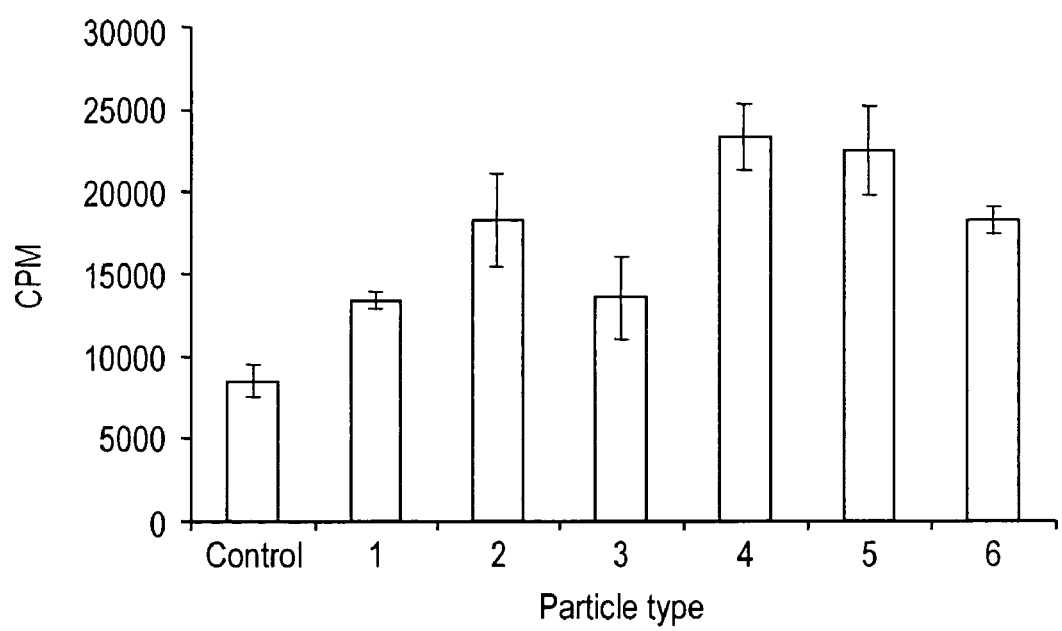
FIG. 7 depicts the effect of the present synthetic materials on proliferation of human osteoblast-like cells (MG-63) compared to control.

(b) Effect on phenotype expression and growth markers: The effect on the phenotype expression and growth markers of human bone-derived osteoblasts was studied by incubating $10^5$ cells/well/ml in the presence or absence of the materials at 37° C., 5% $CO_2$ for 5 days. Total RNA was isolated and specific transcript levels for: osteocalcin (OSC), alkaline phosphatase (AP), collagen type I (Col 1), osteopontin (OSP) and growth markers cyclin D1 (CD1) and CDk5 were determined by reverse transcriptase polymerase chain reaction (RT-PCR). The levels of OSC mRNA were low and expression was not detectable in osteoblasts incubated in control medium alone. Incubation with four different preparations enhanced OSC expression to detectable level (FIG. 7). OSC is documented to play a critical role in mineralization.

FIG. 7 depicts the effect of the present synthetic materials on proliferation of human osteoblast-like cells (MG-63) compared to control. All the materials, especially (2), (4), (5) and (6) caused increased cell proliferation compared to control. (1) and (6) have similar F concentrations, (1) has lower Mg and Zn concentrations.

FIG. 8 shows the effect of the present synthetic materials on the phenotype expression: osteocalcin, OSC; alkaline phosphatase, AP; collagen type I, Col I; and osteopontin, OSP and growth markers: cyclin D1 (CD 1) and CDk4. OSC becomes detectable from materials (4), (5) and (6). The expression for OSP is stronger for materials (4), (5) and (6). The materials used for both tests: (1) Mg/Zn/F-BCPa, (2) Mg/CHA, (3) Zn/CHA, (4) CHA, (5) CFA, and (6) Mg/Zn/F-BCPb. (1) and (6) have equivalent levels of F and $CO_3$, Mg and Zn levels lower in (1) compared to (6). The levels of Mg in (2) and that of Zn in (3) are equivalent to that in (6). The levels of F n (1), (4) and (6) are similar and the levels of $CO_3$ in (10 to (6) are similar.

FIG. 9 shows the effect of BCPs on proteoglycons expression of human osteoblasts. Analysis of proteoglycan transcripts showed no distinct pattern in versican expression whereas decorin expression appeared to be modulated by the CaPs. Biglycan expression was profoundly increased by CaPs containing Mg and F.

Preparation and Characterization of Unsintered and Highly Sintered (Ceramic) Materials Incorporating Mg, Zn, and F in a Calcium Phosphate Matrix. The materials will be designated herein as Mg/Zn/F-BCP. BCP will consist of an intimate mixture of β-TCP (Mg- and Zn-substituted) and carbonate apatite, (Mg-, Zn- and F-substituted). A material with Zn. Mg and F in a calcium phosphate matrix can be prepared. (Mg, Zn, F and Ca have been separately associated with bone formation, bone resorption, biomineralization and bone repair).

Studies on synthetic and biologic apatites (mineral phases of enamel, dentin and bone) using a combination of analytical techniques (x-ray diffraction, infrared spectroscopy, chemical analysis) demonstrated that biologic apatites (the mineral phases of enamel, dentin, cementum and bone) are not pure hydroxyapatite, $Ca_{10}(PO_4)_6(OH)_2$ (stoichiometric Ca/P molar ratio, 1.67) but are associated with minor constituents (most important of which are magnesium and carbonate) and trace elements. Therefore, biologic apatite such as bone apatite, may be more accurately described as carbonate apatite, approximated by the formula:

$(Ca,Mg,Na)_{10}(PO_4,CO_3,HPO_4)_6(OH,Cl,F)_2$ where Mg, Na and $CO_3$ are minor constituents and Cl and F may be present in trace amounts. Substitutions or incorporation of different ions in the apatite lattice cause changes in properties: lattice parameters, crystallinity (reflecting crystal size or perfection), and solubility. For example, partial $CO_3$-for-$PO_4$ substitution (coupled with Na-for-Ca substitution) or partial Mg-for-Ca substitution causes an increase in solubility and decrease in crystallinity. Mg and $CO_3$ have synergistic effects on the properties of apatite. F-for-OH substitution causes a decrease in solubility and increase in crystallinity of synthetic and biologic apatite and promotes formation of less Ca-deficient synthetic apatites. Pure β-TCP cannot be obtained from solution. However, when Mg or Zn ions are present, Mg- or Zn-substituted β-TCP are formed. The formation of partially substituted Mg or Zn in apatite or in β-TCP or Mg- or Zn-containing amorphous calcium phosphate (ACP) depends on the solution Mg/Ca or Zn/Ca or (Mg+Zn)/Ca molar ratios.

Mg- and Zn-deficiencies have been implicated as risk factors in the development of osteoporosis. Separately, Mg, Zn or F has been recommended for osteoporosis therapy. Also, separately, these ions have also been shown to promote bone formation and increase bone mass. In rats, at the biologic apatite crystal level, Mg supplementation was shown to cause the formation of smaller bone apatite crystals and smaller enamel apatite crystals while F-incorporation in bone from the drinking water caused the formation of larger and less soluble bone apatite crystals. F has been shown to consistently increase bone mass. However, other studies have reported increased bone fracture with prolonged use of F compounds. F was shown to affect the orientation of collagen and decrease the level of collagen synthesis, modify bone matrix components and was associated with abnormal mineralization. On the other hand, Zn ions were shown to increase collagen and DNA synthesis.

The material of the present invention by combining relatively optimum concentrations of F, Mg and Zn ions in a calcium phosphate matrix combines the beneficial effects of F of these ions on the bone mineral (increasing crystallinity and decreasing solubility) and of Mg and Zn on the organic matrix components thus minimizing deleterious effects of Mg and/or Zn on the bone mineral or and deleterious effect of F on bone matrix components. In addition, since these ions appear to act additively or synergistically, the dose for each ion can be reduced to a level that will not be harmful after prolonged use.

Preparation and Characterization of Uncalcined or Unsintered Material Incorporating Mg+F (M/F-BCP), Zn+F (Zn/F-BCP), and Mg+Zn+F (Mg/Zn/F-BCP) in a Calcium Phosphate Matrix.

(BCP- describes biphasic calcium phosphate (BCP) preparation consisting of a mixture of β-TCP (Mg or Zn-substituted) and carbonate apatite (Mg-, Zn and F-substituted).

Materials: Reagent grade chemicals (Fisher Scientific) and deionized distilled water are used.

Synthesis: For this study, a series of Mg/F-BCP, Zn-BCP, Mg/Zn/F-BCP is prepared. The BCPs, consisting of intimate mixtures of F-, Mg- and/or Zn- substituted carbonate apatite and Mg- and/or Zn-substituted β-TCP, are obtained by precipitation. The method is by the dropwise addition of solution A (containing Ca and Mg and/or Zn), into a stirring solution B: containing phosphate (P), carbonate (C) and fluoride (F). Reaction temperature, 95° C.; initial reaction pH, 7.5 or 8.5; digestion period after addition is completed, 3 hrs. The precipitate obtained is washed with double distilled water, dried in the drying oven at 80° C. Some of the preparations are sintered at 600° C. or 800° C. The desired concentrations of Mg, Zn and F in these preparations is obtained by adjusting the Mg/Ca and/or Zn/Ca molar ratios in solution A and F/P molar ratios in solution B. The solution C/P is kept constant at a certain ratio that will give 6 wt % or 10 wt % $CO_3$ in the apatite. For the Mg/F-BCP or Zn/F-BCP, the solution F/P is adjusted to obtain the desired F concentration in the BCP. Two levels of F (less than 1 wt % and more than 2 wt %) are initially prepared. For the preparation of a series of Mg/Zn/F-BCP a factorial design or Taguchi design for optimum economics of reducing variation is used. The level of one element is varied, while the levels of the other elements are constant.

For the initial experiments, target concentrations for Mg, Zn and F in the Mg/Zn/F-BCPs were as follows:

Mg: 1 to 5 wt %; Zn: 2 to 10 wt %; and F 1 to 3 wt %. These concentrations provide the appropriate doses such as those used by studies on the separate effects of these ions.

Characterization. The materials are characterized using x-ray diffraction (XRD) for lattice parameters of the apatite and β-TCP components of the BCP (to ascertain substitutions) and crystallinity (crystal size), infrared spectroscopy (FT-IR), scanning electron microscopy (SEM). Ca, Mg, Zn, and P analyses using ICP; and F analysis (using F-ion selective electrode); density, specific surface area and porosity. (Analytical method and the method for determining dissolution properties are described infra).

Preparation and Characterization of Ceramic (Highly Sintered) Materials.

Mg/F-BCP, Zn/F-BCP or Mg/Zn/F-BCP are prepared by mechanical mixtures of Mg-TCP and/or Zn-TCP with CFA. Zn-TCP is prepared according to a method developed by Ito. Briefly, the method consists of preparing a suspension of calcium hydroxide (prepared using calcium oxide obtained by heating calcium carbonate at 1000C) to which is added dropwise, zinc nitrate hexahydrate (0.5 mol/L) and phosphoric acid solution (0.05 mol/L) at room temperature and allowed to digest for 48 hours. The precipitate is filtered, washed and sintered at 850 C. Pure Zn-βTCP containing 0.6 to 6.0 wt % Zn has been obtained by this method. Mg-TCP is prepared in the same way, except using magnesium nitrate hexahydrate reagent. Process parameters including reaction pH, speed of addition of phosphoric acid, stirring speed are optimized. The precipitate is filtered, washed, dried and heated at 850° C. for 1 hr followed by XRD analysis of the heated precipitate. Optimization is carried out until pure Mg-β-TCP (Mg content, 10 mol %) is obtained. 151 g CaO, 230 g 85% $H_3PO_4$, 77.6 g $Mg(NO_3).6H_2O$ and 8 L of pure water will produce about 100 g of Mg-β-TCP powder. CFA is prepared according to the method of Bonel and Montel except for the use of NaF or $NH_4F$ instead of $CaF_2$. Commercially available carbonate hydroxyapatite (CHA) with a $CO_3$ content of 12 wt % is reacted with NaF or NH4F in a temperature range of 200 to 800° C. with and without water vapor, and with and without $CO_2$. Reaction products are characterized using XRD, IR and ICP (Ca, Mg, Zn, P analysis). F content is determined by lanthanum/alizarin complexone method.

Statistical analysis of data: Results from XRD, FTIR, ICP, are examined with t-test and ANOVA to establish equivalency of similar preparations.

Determination of the Short- and Long-term Dissolution Properties (Release of Ca, Zn, Mg and F Ions with Time) of Mg/Zn/F-BCP Materials.

Studies of in vitro dissolution properties in acidic buffer reflect osteoclast degradation and are predictive of in vivo degradation and release of Mg, Zn, F, and Ca ions from the experimental Mg/Zn/F-BCP materials. Dissolution rates of bone mineral obtained from treated animals are lower than those from controls (untreated). Treatment results in compositional changes in the bone mineral making it less susceptible to acid challenge (resorption)

It has been demonstrated that an acidic microenvironment is fundamental to the resorptive process by the osteoclasts. Therefore, in vitro dissolution properties of the Mg/Zn/F-BCP materials under acidic conditions is predictive of in vivo degradation of these materials. For example, β-TCP shown to be more soluble than HA in vitro was also shown to have greater degradation in vivo. The rate of release of the essential elements (Mg, Zn and F) obtained in vitro gives an insight into their rate of release in vivo.

Results from the in vitro dissolution study of experimental synthetic materials provides information on the rate of release of Mg, Zn, F, Ca and P from the Mg/Zn/F—BCP materials and give insight into their release and availability in vivo. The dissolution is affected by the following factors: composition (the greater the F content, the lower the dissolution rate); calcination or sintering temperature (sintered materials have a slower rate of dissolution than the uncalcined or unsintered materials), particle size, porosity and surface area and possibly physical form (e.g., powder vs. discs). The slow release of these ions from the Mg/Zn/F-BCP materials avoids the side effects observed for the fast releasing materials such as those reported for NaF. This results in changes in bone mineral composition and properties making it less soluble.

Short-Term Dissolution Eexperiments:

Materials and methods: Dissolution experiments are made with well-characterized Mg/Zn/F-BCP materials in the form of powder or pressed into discs. The specific surface area, porosity and particle size of each sample are comparable. Discs are prepared by pressing with a hydraulic press using IR KBr pellet maker. Dissolution properties are determined in acidic buffer solution (0.1M NaAc, pH 5.00, 37 C, solid\solution ratio, 25 mg/100 ml buffer) using a pH- stat and the release of Ca onto the buffer with time (4 h) monitored using Ca-ion specific electrode. Also, at time intervals of 5, 10 min, 30 min, 60, 120 and 240 min, 2 ml aliquots of the buffer solution are pipetted out and Zn, Mg, Ca and P of the aliquots are analyzed using inductive coupled plasma (ICP) and F are analyzed using F-ion selective electrode as described infra. The average values for the elements from 3 or more separate experiments (depending on the variance) are reported. The initial rate of release of each ion, $Ca^{2+}$, $Mg^{2+}$, $Zn^{2+}$ or $F^-$, from the material is calculated from the dissolution curves represented by the amount of ions released as a function of time. For example, the $Ca^{2+}$ release curve as a function of time, as with the other ion curves, is theoretically logarithmic and is easily fit by nonlinear regression (to smooth out anomalies) and its derivative, $d[Ca]/dt$, can be extrapolated to time, $t=0$. The value $d[Ca]/dt]_{t=0}$ is the initial rate of release of Ca from the material. The $d[Ca]/dt$ at various t's gives the total Ca released.

Dissolution experiments are also made on characterized bone mineral following the procedure described above. (Characterization includes determination of crystallinity (crystal size) and composition) of the bone apatite).

Long-Term Dissolution Experiments

Discs of Mg/Zn/F-BCP materials are prepared as described above. The discs are immersed in 100 ml acidic buffer solution (0.1M NaAc, pH 5.00, 37 C, solid/solution ratio, 300 mg/100 ml) for 8 days. Every 2 days, the pH of the solution is measured and 2 ml of the solution is pipetted out and analyzed for Zn, Mg, Ca and P using ICP and for F using F-ion selective electrode. The mean average values of the elements from 3 or more separate experiments (depending on the variance) are reported.

Statistical Analysis and Evaluation of Results

Initial dissolution rates at $t=0$, and total ions released for each of the ions (Ca, Mg, Zn, and F) for preparations of various compositions are treated with analysis of variance (ANOVA) and t-tests to discern significant differences ($p \leq 0.05$). Multiple determinations ($n=6$) for each evaluation are made and the values are expressed as means, standard deviations and coefficient of variation for each type of determination. Pearson's correlation is used to show the relationship between various ion release for a given type of preparation in case of the synthetic materials and for various treatment materials in the case of the bone mineral specimens.

Determination of the In Vitro Cell Response to the Mg/Zn/F-BCP Materials Using Osteoblast-Like Cells, Osteoclast-Like Cells from Rat and Human Bone Marrow.

Mg, Zn, F simultaneously present at optimum concentrations in a calcium phosphate system (Mg/Zn/F-BCP materials) enhance osteoblast activity (bone formation) as well as inhibit osteoclast activity (bone resorption) in vitro to a greater degree than when present separately. Cell response to materials with combined incorporation of Mg, Zn and F is more favorable than to materials incorporating these ions separately.

Bones are constantly being remodeled throughout life. Under normal conditions, bones are being dissolved by osteoclasts and rebuilt by osteoblasts under exquisite regulatory control. In pathologic conditions such as osteoporosis, the tightly controlled bone remodeling process is disrupted and osteoclast activity outpaces bone production by osteoblasts. Laboratory models that can characterize the behavior of osteoclasts and osteoblasts at the cellular and molecular level provide critical insights into the pathophysiology of bone remodeling. In vitro cell models are important tools that address this problem. Osteoblast-like cells that exhibit characteristics of normal osteoblasts including synthesis of bone matrix component: collagen type I, osteocalcin, osteopontin and osteonectin help evaluate the effects of Mg/Zn/F-BCPs on cellular events involved in bone formation. Similarly, osteoclast-like cells derived from the bone marrow help clarify the effect of Mg/Zn/F-BCPs on bone resorption. In vitro cell models have also been instrumental in screening various agents and biomaterials for clinical application in a cost-effective way.

Separately, Mg, Zn or F ions have been shown to affect bone cell activities in vitro and promote bone formation in vivo. One isolated report indicated that Mg stimulated osteoblast proliferation in vitro. No recent in vitro studies to date are available on the effect of Mg on osteoclast-like cells. In vivo, Mg depletion was shown to lead to reduction in bone formation and bone volume. Zn was reported to inhibit osteoclast-like cell formation and a significant inhibition of osteoclastic bone resorption at concentrations as low as $10^{-14}$. This is considerably lower than required for inhibition by Ca. Zn deficiency was shown to impair collagen biosynthesis. In vitro F added in cell culture media was shown to directly stimulate proliferation and alkaline phosphatase activity of bone forming cells while others report no effect on proliferation of human osteoblastic cells.

Materials: Materials, which have been characterized in terms of composition and particle size, density, porosity and surface area, are used in this study. The particle size for each type of material is standardized to make the comparison meaningful since particle size larger than cell size could show promotive effect on cell proliferation while smaller particle size of the same composition could show cytotoxicity. The well-characterized materials include F-substituted carbonate apatite (CFA), Mg/F-BCP, Zn/F-BCP and Mg/Zn/F-BCP.

Part 1: For the determination of osteoblast response to Mg/Zn/F-BCPs of various compositions in primary cultures, osteoblast-like cells derived from human trabecular bone are used. Details of the isolation procedure and culture are described below. The cells are plated at $1 \times 10^5$/ml onto 1.5 cm wells and then exposed to different preparations and concentrations of Mg/Zn/F-BCPs and control medium at 37° C., 5% $CO_2$, at different time intervals. Cells are incubated for days to determine proliferative indices; EMC component production is determined after 2-wk incubation period. To insure the reproducibility and provide statistically reliable data, four separate experimental runs are carried out for each test material with three replicate samples for analysis. The effect of these test materials on the cell model described above is assessed using assays for: (1) proliferation, (2) osteoblast phenotype markers: alkaline phosphatase, collagen type I, ostoecalcin and osteopontin, (3) production of bone extracellular matrix (ECM) components: collagen type I and proteoglycans as well as decorin, biglycan, versian and lumican; and (4) morphologic characterization by light and scanning electron microscopy. These methods have been characterized in the laboratory and are being used routinely.

The Effect of the Mg/Zn/F-BCPs on:
(1) Cell proliferation is determined by radiolabeled thymidine incorporation into TCP precipitable DNA and measurement of DNA content.
(2) Osteoblast phenotypic markers for alkaline phosphatase, collagen type I, osteocalcin and osteopontin at the message level is analyzed by reverse transcriptase-polymerase chain reaction technique (RT-PCR)

(3) Production of bone ECM components (collagen type I and proteolycans is determined by radiolabeled proline incorporation andDMB proteoglycan assay. Decorin, biglycan, versican and lumican levels are determined by Western blot analysis using monospecific antibodies.

(4) Cell morphology and structure is assessed by light and scanning electron microscopy.

(Concentrations of Mg, Zn, Ca, P and F in the culture media at the end of the experimental period is determined using the ICP and F-ion selective electrode method.

Analytical Techniques for Part 1:

Cells and cell culture conditions: Normal human osteoblasts exhibiting features of bone tissue osteoblasts are obtained from a number of hospital patients during revision surgery. Pieces of trabecular bone are digested with 0.1% collagenase in a spinner vessel for 24 hrs in 5% $CO_2$ at 37° C. The osteoblast-like cells are maintained in HY cell culture media. Osteoblast-like cells between 2 to six passages (up to two months in culture. Cell concentrations ($1-5 \times 10^5$) are seeded onto 24-well polystyrene plates (Costar Corp., Cambridge, Mass.) for subsequent exposure to Mg/Zn/F-BCPs or control medium alone.

Cell viability and proliferation: The effect of Mg/Zn/F-BCPs on proliferative capacity is analyzed after different time intervals. The purpose of incubating the plates for 3 total days is to determine the effects of Mg/Zn/F-BCPs on osteoblast-like cells during the log phase of growth. Incubation of cells for 7-14 days total days facilitates observation of ECM production after the cells had become confluent and cell growth had reached a plateau. Cells are radiolabeled with $^3$H-thymidine (10 mCi/well) 24 hours before incubation is terminated. DNA synthesis is measured by scintillation counting of TCA precipitable DNA.

Analysis of phenotype expression by evaluation of messenger RNA analysis: Cells are harvested after exposure to Mg/Zn/F-BCPs or control medium alone period. The media is removed from each well and frozen at –70° C. for subsequent analysis of secreted proteoglycans. Total RNA is then isolated and extracted from these cells using the TrIzol reagent method (Life Technologies). A total cDNA library is synthesized using the Advantage RT-for-PCR Kit (Clontech Laboratories, Palo Alto, Calif.) with the oligo (dT) hexamer. The resulting reverse transcnptase product is expanded using the SuperTaq Plus PCR Kit (Ambion, Austin, Tex.). The products are analyzed by gel electrophoresis in 1.5% agarose containing 5 mg/ml of ethidium bromide, and then photographed with UV light excitation. RT-PCR is performed using primers for collagen Type I, alkaline phosphatase, osteocalcin, versican, biglycan, decorin, lumican and osteopontin to determine whether Mg/Zn/F-BCPs support potential production of bone matrix components. For controls, the 28 and 17S RNA and the GPDH housekeeping gene are used to insure equivalent amounts of RNA loading onto agarose gels. Probes are obtained from ATCCICN in the Hopkin's core facility. Messenger RNA levels is determined by densitometry of the bands in agarose gels.

Analysis of bone ECM components: Expression of these osteoblast markers: decorin, biglycan, versican and lumican levels is determined using monospecific antibodies. De novo collagen synthesis is analyzed by immuno-precipitation of radiolabeled proline cell cultures. Secreted and cell-associated radiolabeled immunoprecipitates are subjected to electrophoresis on SDS gels and the newly synthesized collagens are visualized by autoradiography. Osteocalcin levels are verified by ELISA. Collagen type I is also analyzed by Western blot technique. Alkaline phosphatase is measured by enzymatic activity using nitrophenylphosphate as substrate. Proteoglycans is measured by the DMMB assay. Mineralization is assessed using X-ray diffraction and FT-IR.

Analysis of cell morphology and structure: Morphologic characterization is carried out by either retrieving the cells by trypsin-EDTA or by direct fixation of cells onto the plate. Fixed cells are processed and coated with gold palladium for SEM microscopy or appropriately fixed for TEM. Isolated cells retrieved after exposure to the test material are cytocentrifuged onto slides and immunostained to analyze osteoblast markers such as collagen type I, alkaline phosphatase, osteocalcin and osteopontin. Samples are fixed, embedded in paraffin and then processed for immunohistological analysis. Expression of osteoblast markers at the protein level is determined using monospecific antibodies. Bone cell markers such as collagen type I are immunolocalized by using immunoperoxidase staining technique.

For determination of osteoclast response to Mg/Zn/F-BCPs, osteoclast-like cells derived from rat bone marrow is used. Osteoclasts are derived from hematopoietic cells comprised of CFU-GM that differentiate into monocyte-macrophage lineage. These osteoclast-like cells are generated in bone marrow cultures from several species including man, rabbits, rats and mice when propagated in medium containing 1,24-dyhydroxyvitamin $D_3$. These cells have polygonal morphology, contract in response to calcitonin, and express vitronectin receptor. They also express high levels of TRAP, a marker enzyme for osteoclasts. When propagated on bone surface, the osteoclast-like cells create resorption pits that can be visualized by microscopy. Osteoclast-like cells and their progenitors also respond to bone and bone-like components such as apatites. Studies by the applicant and collaborators demonstrated that exposure of rabbit bone marrow cells to apatites generated TRAP positive cells. Osteoclasts produce an acidic environment as they attach to the bony surface resulting in the induction of bone demineralization and matrix degradation. Given optimal time, visible pits can be visualized. The mediators for bone resorption include protons and proteinases and other degradative enzymes that break down the collagen scaffold.

Analytical Techniques for Part 2:

Cells and cell culture conditions: Marrow is flushed from rat long bone and propagated at a cell density of $5 \times 10^5$/plate in DMEM medium with 10% fetal calf serum and $10^{-8}$ M 1,25,dihydroxyvitamin $D_3$ (Hoffman La Roche, Nutley, N.J.) for six days in 5% $CO_2$ at 37° C. On day 6, the adherent bone marrow cells is retrieved, resuspended in the same medium and then enumerated using Trypan blue vital dye to verify the viability and cell number.

Analysis of Phenotype expression by evaluation of osteoclast markers: Osteoclast-like adherent cells are analyzed to verify expression of TRAP by histochemical staining. Osteoclasts have acidic phosphatase activity that is resistant to inhibition by high concentrations (>10 mM) of sodium tartrate. TRAP histochemical technique has been the conventional approach to identify osteoclasts. Visualization of TRAP activity is accomplished by using a napthyl-phosphate as substrate. Cells are also analyzed for the presence of vitronectin receptors using monospecific antibodies. The ability of cells to respond to calcitonin is also studied.

Analysis of resorption pits: Adherent cells resuspended in medium containing vitamin D are replated on dentin slices at different cell density. The cell culture-dentin slices are reincubated from four to six days. Earlier studies indicated that about 4 day incubation is optimal to visualize resorption pits. At the end of the incubation period, cells are removed by dissolution with 2% sodium duodecyl sulphate. The dentin slices are then prepared for scanning electron microscopy. The resorbed surface area is quantified from a grid of 50 mM squares positioned over photomicrographs of three random fields. At least four bone slices are used. Grid intersections over resorption pits are counted. The percent resorption pits over total area is then determined.

Statistical Design, Analysis and Evaluation of Results.

Sample size. The number of cell lines, i.e., sample size to detect differences in the mean results (e.g., proliferative capacity expressed as radiolabeled thymidine uptake) between cells exposed to control and cells exposed to the test materials (Mg/Zn/F-BCPs of different concentrations) is determined by the two-sided pair t-tested. Assuming an 80% power and a standard deviation of 25 for the mean expression under each condition and a conservative estimate for p of 0,2 m we need cells from 4 patients to give an 80% power to statistically detect differences in the means. Statistical aid is obtained using the statistical software pack Query v. 4.0.

Analysis. Regression models are used to test for differences after incubation of cells to Mg/Zn/F-BCPs of different concentrations. Building regression models to analyze the data allows us to control for important covariates that may influence response differences between the effects of the different Mb/Zn/F-BCPs. In order to make proper inferences concerning the regression coefficients and hence obtain better estimates of differences in treatment effects, regression methods are used.

The Effect of orally administered selected Mg/Zn/F-BCP materials (a) on bone properties (density, strength, bone composition) and bone mineral properties (crystallinity, composition dissolution) of adult and aged female and male rats and (b) on the development of osteoporosis induced by calcium- and vitamin D-deficient diet on adult rats.

Oral administration of selected Mg/Zn/F-BCP is more effective than Mg/F-BCP or Zn/F-BCP or CFA in promoting an increase in bone density, bone mass and bone strength.

The degree of improvement in bone properties is influenced by age or sex. The effect of oral administration of the Mg/Zn/F-BCP materials will minimize or prevent bone loss during the development of osteoporosis induced by -deficient diets.

The observed higher incidence of osteoporosis in white vs. black women may be attributed to the higher bone density, better bone quality and lower bone turnover in the latter population. The choice of the rat model is based on the FDA acceptance of this model for the study of osteoporosis and many reported studies using this model. In this study, adult and old (retired breeders), male and female rats are used. Inclusion of male rats is based on the fact the development of age-related osteoporosis affects both male and female in animals and in humans. The choice of adult and old rats (instead of young rats) for the study is based on the reported observation that older rats show greater bone loss when ovariectomized or castrated and increased bone turnover leading to bone loss is observed in adults and old humans.

Deficient diets (Ca-, Zn-, Mg-, F- and vitamin D-deficient diets) have been used to develop osteoporosis in animal models including rats reflecting osteoporosis development in human resulting from nutritional deficiencies. Ovariectomy as a method of inducing osteoporosis is not used in this study so that development of osteoporosis and effect of potential therapeutic agent, Mg/Zn/F-BCP can be observed on both males and females. The inclusion of alveolar bones for analyses (biomechanical, chemical and histomorphometric) is based on reports that the development of osteoporosis may have an effect on alveolar bone loss leading to tooth loss. (The inclusion of tooth specimens (molar) for future analyses (hardness, crystallinity, composition, dissolution) is to determine if the development of osteoporosis makes the tooth mineral more susceptible to acid dissolution (caries).

Results from these experiments shows efficacy of the experimental supplement (Mg/F-BCP, Zn/F-BCP and Mg/Zn/F-BCP) in improving properties of skeletal and oral bones in adult or old male or female rats and the efficacy of such supplement (administered before and after inducing osteoporosis) in minimizing or preventing the development of diet-induced osteoporosis.

Experimental design. The study consists of two phases: Phase 1: determination of the efficacy of orally administered Mg/Zn/F-BCP on improving properties of bone (bone strength, bone density, bone quality) and bone mineral (crystallinity, composition, dissolution rates) and Phase 2: determination of the effect of orally administered Mg/Zn/F-BCP on the development of deficient diet-induced osteoporosis. Phase 1 consists of two experiments: Experiment 4a (involving adult female and male rats) and Experiment 4b (involving old female and male rats). Phase 2 involves only adult female and male rats.

Materials: Selected synthetic Mg/F-BCP (Mg and F), Zn/F-BCP (Zn and F), Mg/Zn/F-BCP (Mg+Zn+F) and CFA (only F) that have been well characterized (using XRD, FTIR, ICP, dissolution) are used for each set of experiments. The concentrations of Mg, Zn and F in the materials for each set are comparable. Materials containing two levels of concentrations, low and high, for each element (Mg, Zn or F) are used. Other sets of experiments use only Mg/Zn/F-BCP compounds. In some experiments, the Mg concentration is varied while Zn and F concentrations remain constant in other experiments, Zn concentration are varied and Mg and F concentrations remain constant. For the initial experiments, selected materials have the following range of concentrations for Mg, Zn and F ions: Mg: 1 to 5 wt %; Zn: 1 to 6 wt %; F: 1 to 3 wt %. The doses (per kg body weight per day) are in the following range: Mg=100 to 300 mg; Zn: 100 to 300 mg; and F: 1 to 3 mg. These amounts are based on Mg, Zn and F separately studied in rats.

Animals and housing: Sprague-Dawley rats, male and female, adult (weighing 160-250 g) and old or retired breeders (weighing 450-525 g) from the Charles River Laboratories are used in the study. NYU veterinarians supervise the protocol and are present at the sacrifice. The animals are housed in the animal facility of New York University College of Dentistry Animal Research Facility under regulated light/dark illumination cycles, constant temperature and humidity. All animals are acclimated to the surroundings and receive normal diet for one (1) week Animal experiments. The animal protocol is reviewed and approved by the New York University Animal Care and Use Committee. The number of animals per group was based on Meta analysis of similar studies Phase 1:

(a) The animals from each sex and age group are divided randomly into 4 groups for each of the two experiments for each study: Experiment 4A (adult female and male) and Experiment 4O (old female and male), each experiment utilizing 50 animals per gender and per age group (e.g., 50 adult female, fa, 50 adult male, ma; 50 old female, fo, and 50 old male, mo).

(b) In each experiment, 10 rats from each group serve as control (receiving no supplement) and 40 rats in each group receive the supplement. The 40 animals per group receiving the supplement are divided into 4 sub-groups (10 in each group): receiving Mg/F-BCP (e.g., fa-MgF); Zn/F-BCP (fa-Zn/F); Mg/Zn/F-BCP (fa-Mg/Zn/F); and CFA (fa-F). All conditions including housing, diet and supplement administration are similar for all experiments. From day 0, the animals receive a nutritionally balanced diet meeting nutritional dietary requirements for rats (American Institute of Nutrition Guidelines and Guide for the Care and Use of Laboratory Animals", Department of Health and Human Services, National Institute of Health, publication 85-23, revised 1985). Each batch of the diet is analyzed for Mg, Zn and F prior to use.

(c) Experimental supplements are given to the specified groups twice a day for a period of twelve (12) weeks. The amount of supplement to be administered depends on the concentration of Mg, Zn and F in the Mg/Zn/F-BCP materials. The supplements are mixed with the food. The amount of food and water used by each animal is monitored daily. Animals have ad libitum free access to water. (Since New York City is fluoridated, the animals are given distilled water). The animals are weighed at the same time of the day once a week.

(d) At the end of 12 weeks, the animals are euthanized by an overdose of sodium pentothal (2-3×s anesthetic dose of 50 mg per kg body weight, 1.5 ml per 100 gms of body weight).

(e) Prior to sacrifice, blood is collected by cardiac puncture under anaesthesia and serum collected is frozen until needed for analyses of Ca, Mg, Zn and F contents.

(f) The right and left femur, vertebrae and jaws are removed, cleaned of soft tissues and bone marrow. Randomly selected vertebra and right femurs from each group are fixed in 70% ethanol for histological and histomorphometric measurements. The left femurs and some of the alveolar bones are used for biomechanical testing and bone density measurements. Some of the bones from femur, jaw and vertebra from each group are defatted using mixture of methanol/acetone, cut into manageable pieces and stored at −20° C. until needed for analysis. Molars from each group are cleaned of soft tissues and stored at −20° C. until needed for analysis Phase 2:
(a) Adult female and male rats are used, 50 from each gender, female (f) and male (m).
(b) Ten (10) rats from each gender group serve as control (receiving no supplement) and 40 rats from each group receive the supplement as follows: Mg/F-BCP (f-Mg/F, m-Mg/F); Zn/F-BCP (f-Zn/F, m-Zn/F); Mg/Zn/F-BCP (f-Mg/Zn/F, m-Mg/Zn/F) and CFA (f-F, m-F).
(c) Similar to Phase 1, step (c).
(d) At the end of 12 weeks (3 months), blood is collected by cardiac puncture under anesthesia and serum collected frozen until needed for analyses of Ca, Mg, Zn and F concentrations.
(e) At the beginning of $13^{th}$ week, deficient diet (Ca-, Mg-, Zn-, F- and vitamin D-deficient diet) is given to all animals to induce the development of osteoporosis. The administration of experimental supplement is continued for the specified groups (except the control). The administration of the deficient diets is continued for 4 months. Food and water intake are monitored daily. The animals are weighed at the same time of the day once a week.
(f) At the end of the study (7 months), blood is collected by cardiac puncture under anaesthesia and serum collected frozen until needed for analyses of Ca, Mg, Zn and F concentrations.
(g) The animals are euthanized by an overdose of sodiumpentobarbital anesthesia.
(h) Same as Phase 1, step (f).

The following analyses are made on specimens from each animal from each group: (1) serum—Ca, Mg, Zn, F and P using ICP; (2) left femurs—mechanical strength; (3) right femur, vertebral and alveolar bone—histomorphometric measurements, bone density, mineral distribution (backscattered electron imaging); elemental distribution (EDS); bone porosity; hardness; (4) bone mineral—crystal size (XRD), composition (Ca, P, Mg, Zn, F), dissolution properties.

Statistical Design, Analysis and Evaluation of Results:

Sample size: It was estimated from meta analysis for similar determinations that ten (10) rats per group would be adequate at a power$\geq$80% to detect significant (P$\leq$0.05) differences expected in the mean values (effect size) of parameters (serum chemistry, bone properties, bone mineral properties) measured.

Statistical analysis: All parameters are evaluated for correlation with materials used. The values are expressed as mean±standard error (SE) For statistical analysis, Student's t test, analysis of variance (ANOVA and NANOVA) with repeated measures, and Pearson's correlation coefficient are used. After verifying normal distribution and homogeneity of variances, ANOVA and Scheffe's multiple comparison tests are used to compare different properties among groups and logarithmic transformation to help assure variance homogeneity are used when appropriate.

Determine the therapeutic effect of selected Mg/Zn/F-BCP materials (administered bv injection) in an ovariectomized rat model bv assessing bone properties (density quality, strength, composition (organic/inorganic ratio), dissolution).

Mg/Zn/F-BCP materials injected in osteoporotic rats increases bone mass and bone density minimizing bone resorption.

Rationale for the ovariectomized rat model. Ovariectomized rats have been used as an animal model for postmenopausal bone loss. The justification for this model is the observed similarities between ovariectomy-induced bone loss in rats and postmenopausal bone loss in humans, e.g., increased bone turnover, greater bone resorption than bone formation, greater loss of trabecular bone compared to cortical bone. In this study, the ovariectomized rats are given deficient diets to accelerate the onset of osteoporosis. Diet deficiency or immobilization and immobilization and calcium-deficient diet have been associated as risk factors for osteoporosis.

Rationale for the use of Mg/Zn/F-BCP materials. Zn-releasing compounds, such as b-alanyl-1-histadano zinc compounds and Zn-TCP are the recent compounds which have been shown to have therapeutic effect on osteoporosis in rats induced by zinc-deficiency. Mg and Zn deficiencies have been reported as risk factors for osteoporosis. F compounds (NaF, monofluorophosphate and slow-releasing NaF) are used in the management of osteoporosis.

The inventive novel material, Mg/Zn/F-BCP materials are found to combine the synergistic beneficial effects of Mg, Zn and F as well as Ca and phosphate ions released from the material to promote bone formation and minimize or prevent bone resorption, resulting in increase in bone mass and less soluble bone apatite.

Materials and Methods.

Materials. Since it has been recently shown that Zn-TCP containing 6 wt % has been effective in increasing bone density, selected Mg/Zn/F-BCP materials containing the following concentrations: Zn-3 wt %; Mg, 3 wt %; F concentrations 1 and 2 wt % are used. Four groups of materials are tested: two groups for calcined and two groups for uncalcined materials with the two levels of F. Ceramic Zn-TCP containing 6 wt % Zn is the positive control. In another study, NaF is used as control.

Animal experiments. Normal females Wistar 5-week old rats (from Crea, Japan) are used. Animal care is provided according to Animal Committee guidelines of Kobe Pharmaceutical University and that of New York University and the animal protocol is approved by the Laboratory Use of Animal Committees of both universities. This study consists of 4 experiments (DI.5a, DI.5b, DI.5c, and DI.5d and uses 60 rats per experiment. The rats are randomly divided into 6 groups (ten per group): G1, G2, G3, G4, G5 and GC. For experiment DI.5a: G1—receive standard Zn-TCP (6 wt % Zn); G2—will receive Mg/F-BCP (3 wt % Mg, 1 wt % F); G3—receive Zn/F-BCP (3 wt % Zn, 1 wt % F); G4—receive Mg/Zn/F (3 wt % Mg, 3 wt % Zn, 1 wt % F); G5—receive CFA (1 wt % F); GC-negative control group, do not receive any material. Experiments DI.5a and DI.5b use uncalcined Mg/Zn/F-BCP materials (prepared and characterized in applicant's laboratory, NYUCD) except for the positive control material, Zn-TCP. Experiments DI.5c and DI.5d use calcined materials (prepared in Dr. Ito's laboratory, NAIST). Zn-TCP material used as the positive control is the same material that has been previously tested and was shown to be effective as therapeutic agent for rats with Zn-deficiency. In other materials, NaF (pharmaceutical grade) is used for comparison with the experimental materials. The materials are injected as suspensions (10 mg of material in saline solution). The animal protocol is based on studies by Otsuka et al. (Injection of experimental materials has been applied to observe new bone formation in osteoporotic patient.

(a) Rats in all the groups are acclimated to the surroundings in the animal quarters and are given regular diet for one week. Food and water intake are monitored daily. Body weight and bone mineral density (BMD) is measured at the beginning and end of the week.

(b) Blood is be drawn from the tail artery from all rats and analyzed for Ca, Mg, Zn, F and plasma alkaline phosphatase and osteocalcin concentrations.

(c) After one week, all animals in each group except group GC, ovariectomized and, in addition, receive a Vitamin D and calcium-deficient diet to accelerate the onset of osteoporosis. The control rats (GC.) receive sham surgery and receive normal diets for the duration of the experiment. All rats have water ad libitum. Food and water intake is monitored daily. The rats are weighed at the same time once a week. BMD are measured once a week. All the animals are kept on this diet regimen for eight weeks.

(d) At the end of nine weeks, four (4) rats from each group are randomly selected from each group and euthanized using an overdose of sodiumpentobarbital anesthesia. Right and left femurs, L1 and L5 vertebra bones, alveolar bones and molar teeth are dissected. All the bones are cleaned of soft tissues including bone marrow. Randomly selected femurs and vertebra from each group are cleaned of soft tissues including bone marrow and fixed in 70% ethanol for biomechanical and histomorphometric measurements. The other bone and teeth specimens are stored in a freezer until required for analysis.

(e) The remaining six rats from each group, except for group GC, are given intramuscular injections on the left or right thigh once a week of suspensions (10 mg material in saline solution) of the selected Mg/Zn/F-BCP materials and given the second diet (deficient diet +0.55% calcium) for ten (10) weeks. Food and water intake are monitored daily. Body weights are recorded and BMD measured at the same time once a week. Blood is drawn from the tail artery before every injection and analyzed for Ca, Mg, Zn and F levels and plasma alkaline and osteocalcin concentrations.

(f) At the end of the study period (19 weeks), body weight is recorded, BMD is measured, blood is drawn from the tail artery for analysis of Ca, Mg, Zn and F concentrations and plasma alkaline phosphatase and osteocalcin concentrations. The rats are euthanized using an overdose of sodiumpentobarbital anesthesia. Right and left femurs, L1 and L5 vertebra bones, alveolar bones and molar teeth are carefully dissected. All the bones are cleaned of soft tissues including bone marrow. Randomly selected femurs and vertebra bones are fixed in 70% ethanol for biomechanical and histomorphometric measurements. The other bones and cleaned teeth specimens are stored in the freezer until required for analysis.

Analyses.

The following analyses are made from each animal in each group: (a) serum—plasma alkaline phosphatase, osteocalcin, Ca, Mg, Zn and F; (b) right femur and lumbar vertebrae: mechanical strength, bone mineral density (using bone mineral densitometer, model DCS-600 Aroka), (c) left femur, vertebra and jawbone—histomorphometric measurements; inorganic/organic ratio (FTIR)., (d) bone mineral—crystallinity (crystal size), composition (Ca, P, Mg, Zn, F)

The Ca, Zn and Mg concentrations are determined using atomic absorption spectrometry (Type 180-70, Hitachi Co); F is determined using F-ion selective electrode. The in vitro data points represent the averages of three measurements each. The monitoring of Zn or Mg levels after injection of the material gives an indication of the release of these ions from the materials and their effect on the calcium levels. Such monitoring also provides information on whether the materials are releasing cytotoxic levels of the ions.

The plasma alkaline phosphate activity is determined using the phenyl phosphoric acid method using UV/VIS spectrometer (Type UV160, Shimadzu Co at 500 nm using commercial measurement kits (Wako Chem Co, Japan). The plasma osteocalcin levels are determined using commercial measurement kits. The data points represent the average of four measurements each. Immunoassays of osteocalcin and bone alkaline phosphatase are currently the most sensitive markers for bone formation in clinical research assessing treatment for osteoporosis.

For histomorphometric analysis, both ends of the right femoral bone are cut and fixed in 70% ethanol. Undecalcified sections are prepared at using the following procedures: the bone is stained with Villanueva bone stain and embedded in methymethacrylate. Each undecalcified block is cut into 500 mm thick sections by cutting vertical to the bone axis using Crystal Cutter slicer with a diamond blade. The sections are ground to a thickness of 150 mm using an ML-150 D.C. speed-track machine (Maruto Co), and reembedded in polyester resin, and finally ground to a thickness of 30 mm using the Speed-track machine. The sections are observed with a light microscope; images are captured using a CCD camera (Sony) and are analyzed histomorphometrically with software, Image-pro (MediaCybernetics, USA) to determine medullary cavity area, cortical bone area and total area of porosity in cortical part. The histomorphometrical data is analyzed using one-way analysis of variance (ANOVA) with independent variable of groups, followed by Fisher's protected least significant difference (PLSD) test.

Analyses

A. General

Characterization of materials: (a) Crystallinity: using X-ray diffraction, XRD, infrared spectroscopy, FT-IR; (b) Composition: using inductive coupled plasma, ICP and F-analyses; (c) Surface area; (d) Morphology: using scanning electron microscopy, SEM; (e) Cell response: in vitro cell culture methods described in Section D1, (f) Dissolution properties.

Determination of properties of bone: (a) Biomechanical properties (bone strength): using four point bending method; (b) Bone density and mineralization pattern of cortical, trabecular and alveolar bone: will be determined using back scattered electron imaging, BSE and image analysis; (c) Bone quality (porosity using SEM; (d) Histomorphometric determinations are made on decalcified and undecalcified stained and unstained sections. (e) Bone composition: organic/inorganic ratio: using FTIR, thermogravimetry, TGA, ashing and distribution of Mg, Zn and F and Ca/P, Mg/Ca in femur (cortical and trabecular) and alveolar bone: using electron dispersive (EDS) analysis; (f) Dissolution properties (Section D1).

Determination of bone mineral properties: Preparation of bone mineral: powdered bone is suspended in ethylenediamine, washed in distilled water and dried. For ICP and F analyses, powdered bone is ashed at 800° C. The following properties is determined: (a) composition and crystallinity: using XRD, FTIR; (b) composition: using FT-IR (carbonate content); ICP (elemental analysis of Ca, Mg, Zn, P); F-ion selective electrode (F content); (c) dissolution properties.

B. Specific Analytical Methods

1. Biomechanical properties: The biomechanical properties of the femur bones are determined using the methods described by others. The mechanical strength of rat femur is determined using a 3-point bending (flexure) test. Kenney et al [88] reported that this test allows 'standardized comparisons across treatment groups even if bones differ in size. Previously frozen rat femurs are thawed and equilibrated in saline at room temperature and kept wet with saline throughout the procedures. The length of the right femur (to the nearest 0.1 mm) and external midshaft diameters (perpendicular and parallel to force to be applied; determines to the nearest 0.001 mm) is measured with an electronic micrometer. The flexure test of the femur is performed with an MTS and Instron Model 5566 Universal Testing Machine (with computer output) using with 50-kg weigh beam, 2.5 mm/minute crosshead speed, and supports set 11 mm apart. Internal diameters of the bone parallel and perpendicular to the breaking force is measured, using a magnifier with embedded measuring scale, after cutting through the bone shaft near the break with a fine-toothed steel saw. Specimens are kept wet during the testing.

Standard mathematical expressions of several mechanical properties are used to calculate from bone dimensions, load applied to the bone during testing, and a tracing of load versus deformation as the load is increased until the bone breaks. Stress and modulus of elasticity is determined from the initial linear portion of the load-deformation curve. Yield stress for the femur is calculated as the force per unit cross-sectional area, at the point where the curve ceases to be linear and plastic deformation began. Ultimate stress is determined similarly, based on measurements at bone breakage under peak load.

2. Bone histomorphometry. Cortical and cancellous bone from vertebra, femur and alveolar bones are analyzed.

Preparation of undecalcified bone sections. Specimens are fixed in 3% gluteraldehyde and then dehydrated in progressive concentrations of alcohol (70-100%) and embedded in a composite of methyl and glycol methacrylate. Consecutive 5-mm sections are obtained at 100 mm intervals by using an Ultramicrotome (LKB 2088) with a diamond knife.

Preparation of decalcified sections. Bone specimens are decalcified in 10% EDTA at pH 7.4. After dehydration, the decalcified bone specimens (vertebra, maxillae, mandibles) are infiltrated with paraffin under vacuum and embedded in paraffin. Alternate cross sections are prepared serially and stained with H&E and Toluidine blue.

2a. Light Microscopy and Image Analysis.

Undecalcified bone sections. Sections are stained with Goldner-Masson trichrome stain and other sections are stained with Toluidine blue and other sections are unstained.

Decalcified bone sections. sections are stained with Trichrome, Toluidine blue and the other section with Haemotoxylin-Eosin (H&E).

For both undecalcified and decalcified sections, the trichrome-stained sections are used to measure the relative proportions of new and old bone, forming, resorbing and inactive surfaces; Toluidine blue-stained sections are used to determine: bone volume/tissue volume, osteoid volume, osteon wall thickness, trabecular thickness, osteoid thickness, porosity, osteoblast surface/bone surface, eroded surface/bone surface, osteoblast number/bone perimeter and osteoclast number/bone perimeter; H&E stained sections are used to characterize cell type and population.

Histomorphometric measurements. The histomorphometric method is based on that described by Eriksen et al Nomenclature, symbols and units are in accordance with those recommended by the American Society of Bone mineral Research. Histomorphometric quantifications of stained sections of cortical and cancellous bone from vertebra and alveolar bone are carried using a computerized semiautomated system image analyzer (Bioquant NovaPrime 6.00.10, Nashville, Tenn.) that uses a microscope (Leitz) and digitizing tablet.The system software allows measurement of perimeter, area, distances and individual counts and performs all calculations and merge data from multiple sections for each specimen. Fields from each slide are examined. An optical grid is used to identify an index field, and subsequent fields are selected sequentially from the bone compartment by moving the microscope stage in a stepwise fashion across the diagonal axes of the medullary cavity.

Electron microscopy back-scattered imaging (BSE) and image analysis are used to determine mineral distribution or mineralization pattern, bone formation, and bone density.

Quantitative Backscattered electron (BSE) imaging (measuring mineral percentage) method (including parts of the specimen preparation) used in this study is based on the methods described by Roshger et al. This technique is used for measuring microscopic mineral content variations (ormineralization patterns) in bones (cortical, trabecularfemur and vertebral bones and alveolar bone) to show the effect of systemic Mg/Zn/F-BCP. Depending on SEM operating conditions, the volumetric resolution of BSE images in bone ranged from 0.07 to 137 $\mu m^3$, which is considerably better than the highest resolution in microradiography. The BSE signal converts into a digital one obtained by BSE imaging of the corresponding bone area. In this way, the gray level in calibrated BSE images of bone tissues has a positive correlation with bone mineral content and density: highly mineralized (white) and less mineralized (gray) areas.

Sampling and Specimen Preparation: Bones (femur, vertebra and alveolar bone) are defatted using a mixture of reagent grade methanol and chloroform, 70:30 v/v and dehydrated in a graded series of ethanol. The specimens are then embedded in polymethylmethacrylate (PMMA), and cut into small cubes with a band saw. Using an Isomet (Buehler), the cubes are then cut from the desired areas. The blocks of femur, vertebra, and jaw are cut from the middle of the bone and perpendicular to their long axes. The block is then ground and polished using 0.5 im diamond to an optical finish. This procedure is done carefully to avoid generating scratches and polishing reliefs that would generate a topographical contrast and thus interface with the material contrast in the BSE images. The surface of blocks are then lightly coated with gold using a sputter-coating evaporator. A JEOL 5400 SEM equipped with a solid-state BSE detector is used in this study. SEM operating conditions: 30 kV accelerating voltage; 15 mm working distance; and 0.75 mA probe current. In each section, seven equidistantly spaced microscopic fields are analyzed at 200×. BSE images are collected as 512×512 pixel with 256 distinct gray levels. The weighted mean gray level (WMGL) of each image are calculated following this equation black/white image where the intensity (gray level) of any pixel in the image is proportional to the mean atomic number of the corresponding location on the target material. It had been shown previously that there exists a linear positive correlation between local weight concentration calcium (wt % Ca) as measured by X-ray microprobe analysis and gray levels as: $WMGL=3A_i GL_i/A_t$; where i is between 6 to 255; $A_i$=area of ith graylevel; $GL_i$ ith gray level; and $A_t$=total area imaged. This provides a mean value for the back-scattered signal, independent of porosity (black pixels i=0 to 5). WMGL are calculated using an image analysis system (Leica Q500IW Imaging Workstation). To ensure instrument stability, BSE-image WMGLs are calibrated at 20 min intervals using a magnesium alloy (99.8% pure; 93% Mg, 6% Al, and 1% Zn; Johnson Matthey Inc., Seabrook, N.H.) and diamond (99.9999% pure, Johnson Matthey) as calibration standards.

X-ray Diffraction (XRD) analyses: on powdered samples is employed using Philips X'Pert with built in computer programs and JCPDS files for material matching and identification. Data on lattice parameters (using KCl as internal standard) and crystallinity (crystal size) are obtained. Crystal size measurements are made from the broadening of the diffraction peak using the Scherrer equation. Approximate β-TCP/HA ratios are calculated based on a calibration curve of ratios of intensities of largest peaks for β-TCP and HA in mechanical mixtures of varying β-TCP/HA ratios. Quantitative ratios are determined using a subtraction method described previously. XRD analyses at NAIST on powdered samples are made using Rigaku RIT 2400 unit coupled with a Dell computer using software for control, data collection and data analysis.

4. Infrared absorption (IR) analyses are employed using a Perkin-Elmer 983 G quadruple grating spectrometer with range from 5000 $cm^{-1}$ to 180 $cm^{-1}$ with up to 0.5 $cm^{-1}$ resolutions. Absorption spectra are collected on powdered samples mixed with KBr (IR grade) (1 to 2 mg sample/300 mg KBr) and pressed into a pellet at 12,000 psi. Deconvolution of IR peaks and definition, using second derivative techniques, is accomplished using software prepared in this laboratory. Scanning range, 4000 to 400 cm, normal slit, normal scanning speed. (a) purity—whether the material is uni- or multi-phasic; (b) identity from the presence of characteristic features of the vibration bands of functional groups, e.g. $CO_3$, $HPO_4$, $PO_4$ (from the inorganic component in the case of bone or from apatite or β-TCP phase, in the case of synthetic materials), $NH_2$ (from the organic component) on vibration band characteristics. (Precision: IR absorbance line position "0.5 $cm^{-1}$. Band resolution, 2 cm).

Determination of carbonate/phosphate ratio: is calculated from the integrated areas of the absorption bands of the phosphate ($PO_4$) groups at 1000 to 1200 $cm^{-1}$ and of the carbonate ($CO_3$) groups at 1400 to 1550 $cm^{-1}$ and 800 to 900 $cm^{-1}$ and calculating the wt % $CO_3$ from standard curves obtained from a series of carbonate apatite of known $CO_3$ concentrations determined by Conway diffusion analyses. (Precision, ±5%).

Determination of inorganic/organic ratios: is calculated from the integrated areas of the absorption bands of phosphate ($PO_4$) groups at 900 to 1200 $cm^{-1}$ and of the amide (—$NH_2$) group at about 1585 to 1725 $cm^{-1}$.

Fourier-Transform Infrared. FT-IR Microsopy. A Nicolet 550 FTIR microscope is used equipped Research-Plan Zeiss microscope with liquid nitrogen mercury cadmium telluride detector and video camera coupled to an IBM desktop computer control and data collection. In NAIST, FT-IR analysis is made on a Jasco FTIR 350. To observe sections under the microscope: the mineralized tissues are dehydrated in a graded ethanol and embedded into methymethacrylate+butyl methacrylate (similar to sample preparation for SEM). The samples are then cut to 8 μm thickness using an ultramicrotome (LKB 2088) with a diamond knife. The section is mounted on a $BaF_2$ disc for analysis under the microscope. This instrument allows the detection, by both transmission and reflectance spectroscopy of both mineral and matrix characteristics within the mineralized tissues. FT-IR and FT-IR microscopy is now widely applied in the studies of mineralized tissues.

Scanning electron microscopic analyses (SEM) and energy dispersive X-ray analysis (EDS). SEM and EDS are performed on an JEOL 5400 with backscatter device and EDS with EVEX Laboratories analyzer and liquid $N_2$-cooled Si (Li) crystal detector. SEM is used to determine morphology, porosity, and surface characteristics. For SEM studies of Mg/Zn/F-BCP preparations, the particles are spread on the carbon adhesive tabs, mounted on the aluminum holders and coated by carbon or gold. To observe calcified tissues (which are not decalcified), the samples are fixed for 3 days in a mixture of 5 ml gluteraldehyde 4%+5 ml sodium cacodylate buffer+20 ml distilled water. They are then dehydrated for 3 days in each of the graded ethanol (80%-95%-100%). The samples are then impregnated for two days into a mixture of ½ alcohol+½ methylmetacrylate (MMA). The samples are embedded in a mixture of MMA+butylmetacrylate. Polymerization is allowed to take place at 60° C. for 24 hrs. The surfaces of the blocks are polished to a smooth surface, using different grades of abrasive papers and diamond paste. To observe the calcified tissues without embedding, the organic components are dried using critical point.

Electron dispersive analysis (EDS): The specimens are cemented with carbon glue and coated with carbon. Calibration is performed before each analysis using Al and CuKá peaks. The system is programmed to identify F, Mg, Zn, Ca and P peaks, to subtract a background spectrum from the spectrum of interest and to print out the values of the appropriate peaks. The EDS is performed using a EVEX microanalysis system connected to SEM. Data is collected over 100 seconds. Ca/P, Mg/Ca, Zn/Ca and F/P of standard calcium phosphate preparations (HA, unsubstituted and Mg- or Zn-substituted b-TCP, F- and $CO_3$-subsituted apatites) with known composition from ICP and F analyses are used to calibrate the values obtained by EDS. EDS analytical method is a method of good precision and accuracy and allows the determination of elemental distribution in different sites in the same bone specimen. (Detection limit, 0.1 to 0.5%).

Transmission electron microscopy (TEM). TEM and electron diffraction are performed at 100 kV with a JEOL 100CX. TEM allows the visualization of the crystal planes from which crystal perfection, grain boundaries between crystals, and crystal orientation can be determined and crystal size can be measured. In addition to determining crystal properties, TEM is used to observe the organic components of the calcified tissues and their interface with biological crystals.

Sample preparation: Fresh calcified tissues is cut to 1×1×1 mm pieces and fixed in 4% glutaraldehyde for one hour, then dehydrated for 20 min in each of the graded ethanol. Dehydrated specimens are impregnated in LR White (½100% ethanol) for one hour, then placed in embedding capsules and embedded in 100% LR White and polymerized in the oven at 55° C. for 24 hr. The embedded sample is cut into ultra thin sections (90 nm thick) using an ultramicrotome (LKB) with a diamond knife. The sections are then mounted on a 100 mesh copper grid and enforced by a thin layer of carbon (1 nm). To observe the organic components, ultra thin sections are mounted on gold grids, contrasted with uranyl acetate, washed with distilled water and dried at room temperature.

Electron diffraction: By indexing the diffraction patterns, symmetry, orientation and defects of the crystals in the mineralized tissues are identified. To obtain electron diffraction using TEM, the crystal axes are oriented using a double-tilt holder. The patterns are indexed and identified by means of an electron diffraction pattern simulator (CaRIne 3.0) that uses stored crystallographic data for known Ca—P phases. Generated electron diffraction patterns can then be directly compared with observed diffraction patterns.

Measurement of width and thickness of biological apatite crystals: Apatite crystals shown by TEM to be cut perpendicularly to the c-axis are chosen for width and thickness measurements. Dark field images are used in which crystals that strongly scatter the electron beam appear bright against a dark background, so that only the scattered beams from the crystal planes contribute to image formation. Results are expressed as the mean±SD. Comparative study of means are performed using the ANOVA statistical test. Results are considered significantly different when $p<0.05$.

Surface area measurements are made using a Micromeretics Flowsorb 2300. The specimens for specific surface area (SSA) measurements are outgassed at 40° C. and flushed with an ultra dry mixture of helium and nitrogen. The SSA is determined using a mixture of He and $N_2$ gas (70:30) and condensing the $N_2$ on the specimen at liquid nitrogen temperatures. SSA is calculated based on the data those 16 sq. angstroms of condensed monolayer of nitrogen is occupied by one molecule. The areas obtained are adjusted for the mass of the sample to give sq meters/gm sample.

Porosity. Total porosity is obtained with nitrogen/helium porosity isotherms using a Micromeretics Flowsorb #2300 instrument. Distribution of micro- (1 m)-, or meso- (up to 10 u) and macro- (10 to 400 u) porosity and percent porosity (volume percent of the specimen occupied by the pores) is determined. Porosity can also be measured from BSE images using image analyses. Measurements are made on bone segments of similar sizes from the same cortical and trabecular areas of the vertebra from each group.

Density. Bone density on specimens of 3 to 7 mm thickness (measured with an electronic micrometer) of cortical and trabecular bone is determined using AccuPyc 1330 (Micromeritics, Atlanta). Thin sections from cortical and trabecular areas that have been defatted in a large volume of reagent grade chloroform, dehydrated in graded ethanol, are weighed on an analytical balance. Volume of all segments are measured. Density is calculated from the volume and weight measurements of each segment.

Thermogravimetric (TGA-DTA) analyses are made on a Perkin Elmer TGS DTA system. TGA analyses provide information on weight loss as a function of the temperature of heating (for biological materials the loss of the following components is indicated: adsorbed $H_2O$ (60 to 200° C.), organic phase (200 to 400° C.), and $CO_3$ (700 to 900° C.). TGA have been used in the analyses of mineralized tissues and synthetic calcium phosphate.

Inductive coupled plasma (ICP). Concentrations of Ca, P, Mg, Zn, and F in the bone mineral and in the synthetic materials is analyzed using inductive coupled plasma, ICP (Thermo-Jarrel-Ash TraceScan plasma spectrometer is used at NYUCD; Seiko ICP instrument (SPS7800) is used at NAIST). The ICP instrument is a programmable sequential plasma emission spectrometer. The bone mineral obtained by treatment of powdered bone with ethylenediamine or synthetic materials (25 mg) is dissolved in 17% HCl and made up to 25 ml in a volumetric flask with double distilled water. Appropriate standard solutions for Ca (0, 20, 40 pm), Mg (0, 1, 10 ppm), Zn (0, 1, 10 ppm) and P (0, 10, 40 ppm) are prepared from standard solutions (Fischer Scientific). The specimen in solution and standard solutions is pumped through argon plasma excited by a 2 kW 27.12 MHz radio frequency generator. Specific wavelengths are chosen for each element (Ca, 3179A; Mg, 2852 A; Zn 2138 A and P, 2136A). Typical coefficients of variation for Ca, P, and Mg are less than 1ppm in saliva. This great sensitivity and extreme reliability allows easy comparisons using ANOVA or Tukey statistics at the 95% significant level.

Determination of F content: Fluoride (F) analyses of the synthetic and biological materials are made using the specific ion electrode using appropriate standards (0, 10, 20, 40, 50 ppmF). The solution prepared for ICP analysis are used. 1ml of solution is added to 1 ml Tisab 2 and the F concentrations obtained from the standard curve concentrations using F-ion selective electrode (Orion Research Inc, Boston). Results are expressed as % F in bone ash as an average of three (3) separate analyses. (Precision of method:±0.001 ppm F)

Hardness. Knoop Hardness of the femur, vertebra and jawbones are measured using Rumulo IV Alexandra microhardness tester. Ten measurements are made across the width of the cancellous bone. Similarly, ten (10) measurements are made in the cortical bone.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

The invention claimed is:

1. A biomaterial for therapeutic use in treatment of osteoporosis, and for use in bone and fracture repair, comprising: a carbonate-containing calcium phosphate matrix comprising two phases, said matrix incorporating biologically active concentrations of magnesium, zinc and fluorine ions.

2. A biomaterial in accordance with claim 1, wherein said matrix comprises carbonate hydroxyapatite (CHA) and β-tricalcium phosphate (.beta.-TCP).

3. A biomaterial in accordance with claim 1, wherein the magnesium ion is present in an amount from 0.5 to 12 wt %, the zinc ion is present in an amount from 1 to 12 wt %, the fluorine ion is present in an amount from 0.1 to 4 wt %, calcium is present in an amount from 20 to 40 wt %, phosphate (P) is present in an amount from 10 to 20 wt %, and carbonate ($CO_3$) is present in an amount from 1 to 20 wt %.

4. A biomaterial in accordance with claim 1, wherein the magnesium ion is present in an amount from 0.5 to 12 wt %.

5. A biomaterial in accordance with claim 1, wherein the zinc ion is present in an amount from 1 to 12 wt %.

6. A biomaterial in accordance with claim 1, wherein the fluorine ion is present in an amount from 0.1 to 4 wt %.

7. A biomaterial in accordance with claim 1, wherein said biomaterial is particulate.

8. A biomaterial in accordance with claim 1, wherein said biomaterial is highly sintered.

9. A biomaterial in accordance with claim 1, wherein said biomaterial is unsintered.

* * * * *